United States Patent
Naoi et al.

(10) Patent No.: US 9,913,907 B2
(45) Date of Patent: Mar. 13, 2018

(54) RNAI PHARMACEUTICAL COMPOSITION FOR SUPPRESSING EXPRESSION OF KRAS GENE

(71) Applicants: DICERNA PHARMACEUTICALS, INC., Watertown, MA (US); Kyowa Hakko Kirin Co., Ltd., Tokyo (JP)

(72) Inventors: Tomoyuki Naoi, Tokyo (JP); Takeshi Kuboyama, Tokyo (JP); Junichi Enokizono, Shizuoka (JP); Toshihiko Ishii, Shizuoka (JP); Akihiro Tokunaga, Shuzuoka (JP); Kentarou Hatanaka, Tokyo (JP)

(73) Assignees: KYOWA HAKKO KIRIN CO., LTD., Tokyo (JP); DICERNA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 13/943,038

(22) Filed: Jul. 16, 2013

(65) Prior Publication Data
US 2014/0044755 A1 Feb. 13, 2014

Related U.S. Application Data

(60) Provisional application No. 61/671,963, filed on Jul. 16, 2012.

(51) Int. Cl.
| | |
|---|---|
| *C12N 15/113* | (2010.01) |
| *A61K 31/713* | (2006.01) |
| *A61K 47/22* | (2006.01) |
| *A61K 9/00* | (2006.01) |
| *A61K 9/127* | (2006.01) |

(52) U.S. Cl.
CPC ............ *A61K 47/22* (2013.01); *A61K 9/0019* (2013.01); *A61K 9/1272* (2013.01); *A61K 31/713* (2013.01); *C12N 15/1135* (2013.01); *C12N 2310/14* (2013.01); *C12N 2320/32* (2013.01)

(58) Field of Classification Search
CPC ................. A61K 31/713; A61K 47/22; A61K 47/48061; A61K 9/0019; A61K 9/1272; A61K 424/40
USPC .......................... 424/400; 514/44 A; 536/24.5
See application file for complete search history.

(56) References Cited

FOREIGN PATENT DOCUMENTS

| | | |
|---|---|---|
| CA | 2 800 818 | 11/2011 |
| JP | 2-135092 | 5/1990 |
| JP | H2-135209 | 5/1990 |
| WO | WO199851278 A2 * | 11/1998 |
| WO | 00/30444 | 6/2000 |
| WO | 2000/030444 | 6/2000 |
| WO | 2005/121348 | 12/2005 |
| WO | 2008/109516 | 9/2008 |
| WO | WO2008109516 A2 * | 9/2008 |
| WO | 2009/086558 | 7/2009 |
| WO | 2010/115206 | 10/2010 |
| WO | WO2010115206 A2 * | 10/2010 |
| WO | 2011/136368 | 11/2011 |
| WO | WO2011136368 A2 * | 11/2011 |
| WO | 2013/089151 | 6/2013 |
| WO | 2013/089152 | 6/2013 |

OTHER PUBLICATIONS

Mamta Kapoor et al., "Physicochemical characterization techniques for lipid based delivery systems for siRNA", International Journal of Pharmaceutics, 2012, vol. 427, No. 1, pp. 35-57.

* cited by examiner

*Primary Examiner* — Janet L Epps-Smith
(74) *Attorney, Agent, or Firm* — Wenderoth, Lind & Ponack, L.L.P.

(57) ABSTRACT

The present invention provides a composition for suppressing the expression of a KRAS gene, comprising a lipid particle containing, as a drug, a double-stranded nucleic acid having an antisense strand having a sequence of bases complementary to the sequence of at least 19 continuous bases of any one KRAS gene's mRNA of sequence Nos. 1 to 3; and a cationic lipid represented by the following formula (I):

wherein $R^1$ and $R^2$, which are the same or different, are each linear or branched alkyl, alkenyl or alkynyl having a carbon number of from 12 to 24;

$L^1$ and $L^2$, which are the same or different, are each —CO—O— or —O—CO—;

a and b, which are the same or different, are each 1 to 3; and $R^3$ is a hydrogen atom, alkyl having a carbon number of from 1 to 6, or alkenyl having a carbon number of from 3 to 6, and the like.

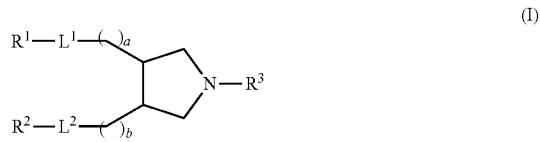

(I)

21 Claims, 6 Drawing Sheets

[Fig.1]
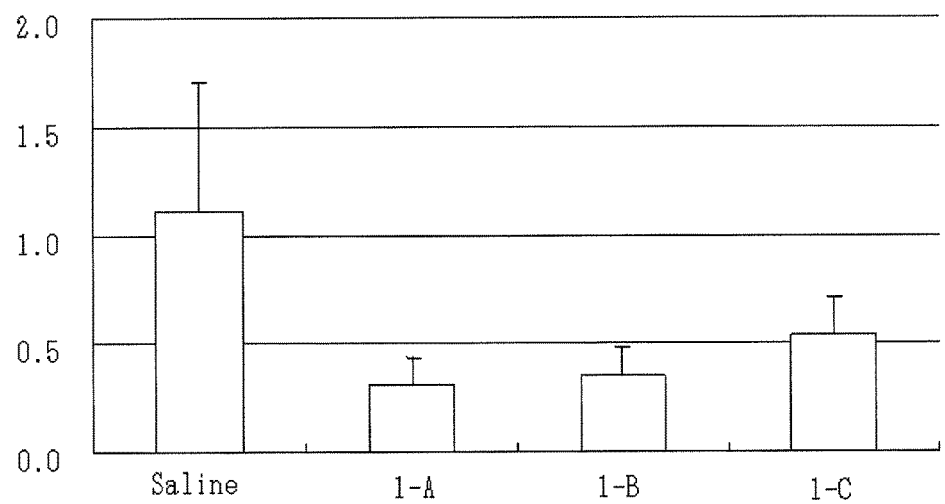

[Fig.2]
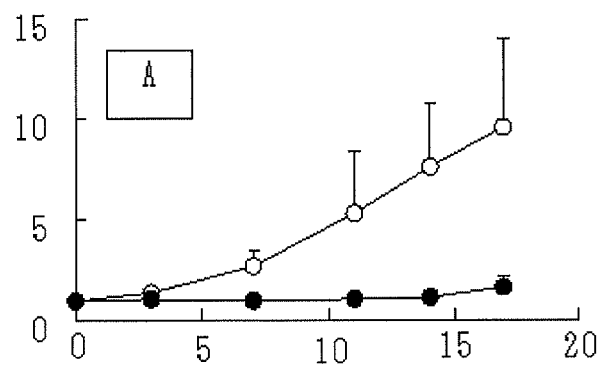
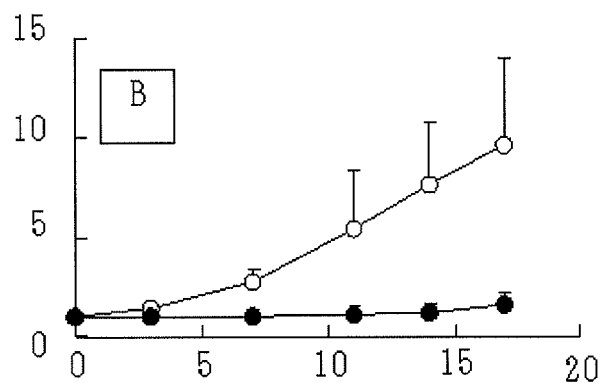
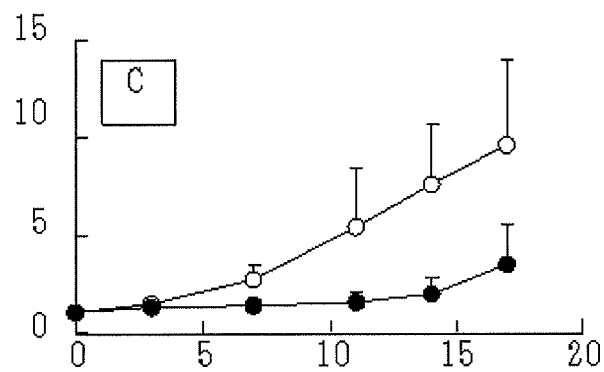

[Fig.3]
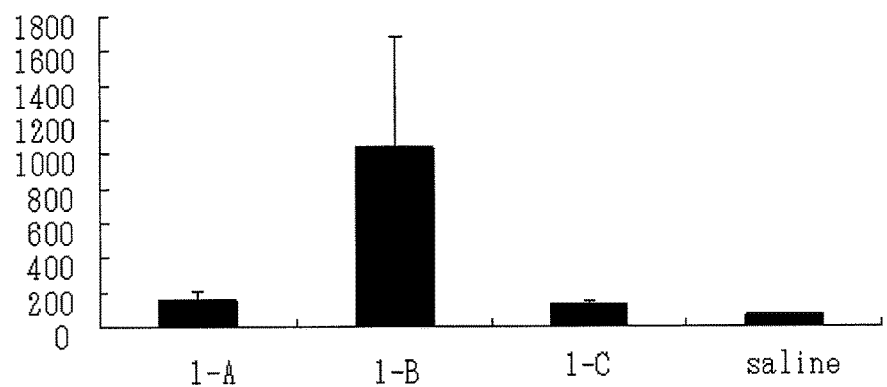
[Fig.4]
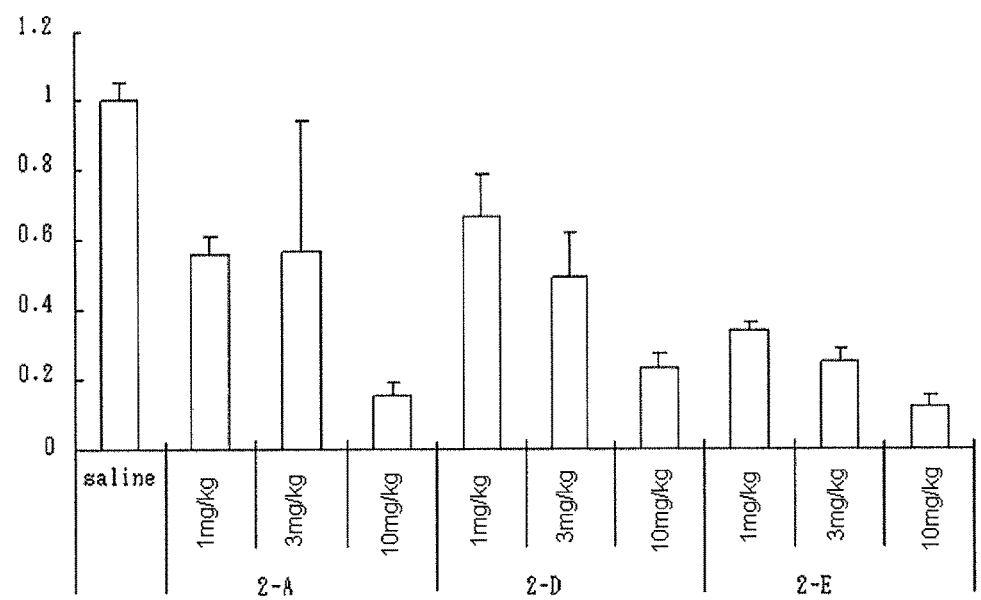

[Fig.5]
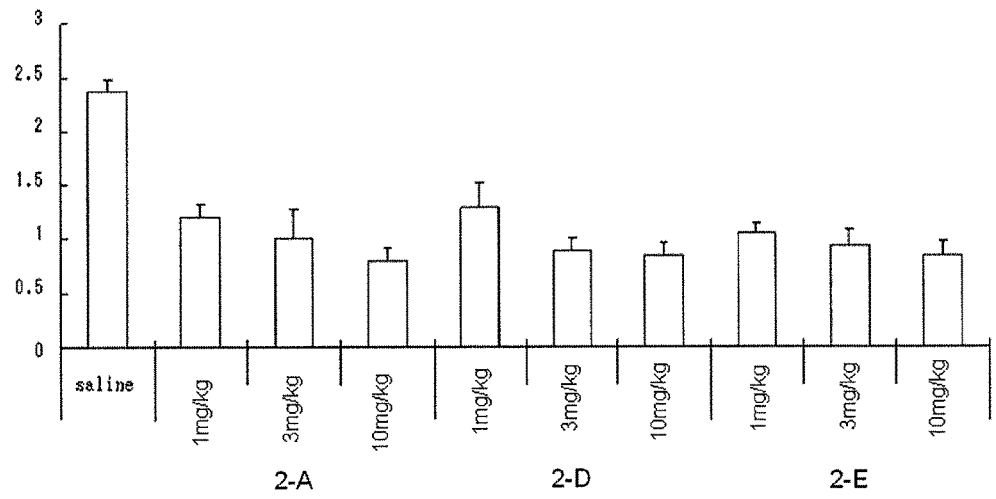
[Fig.6]
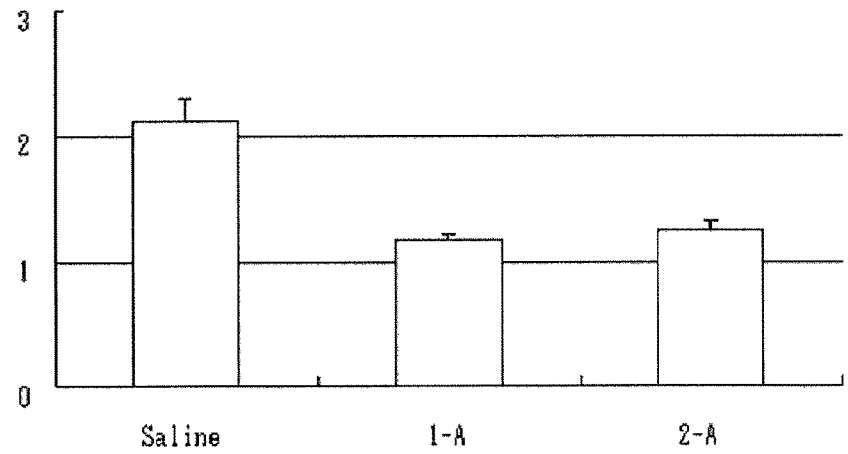

[Fig.7]
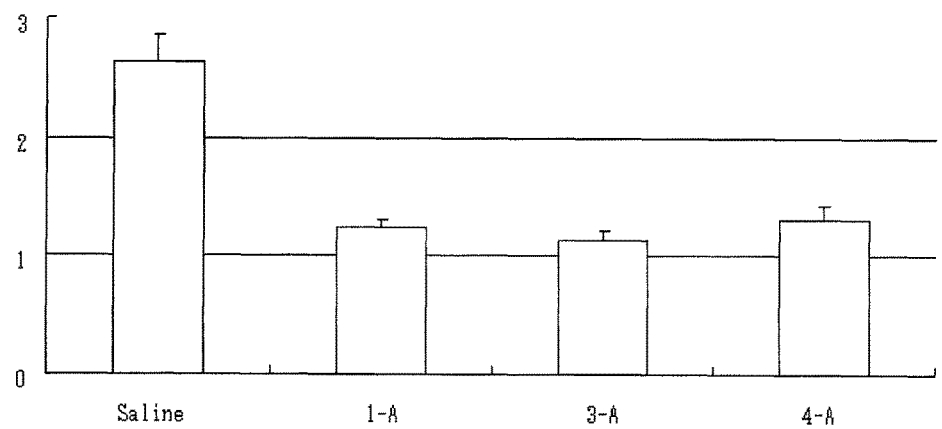
[Fig.8]
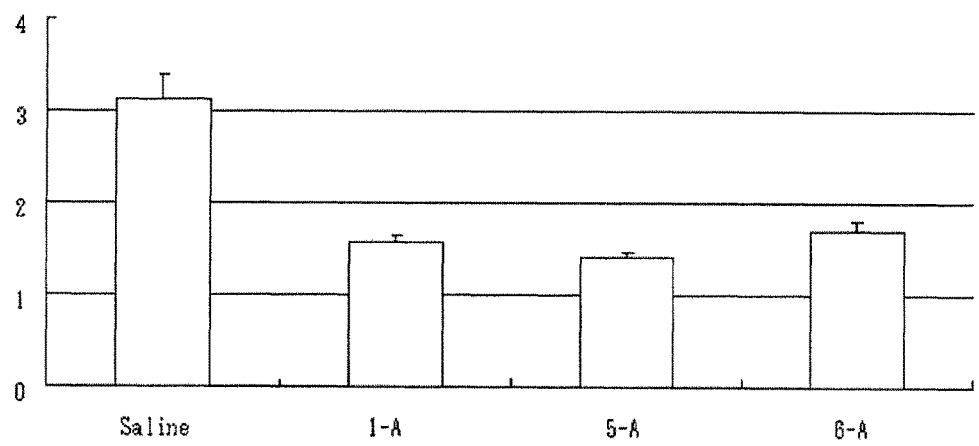

[Fig.9]
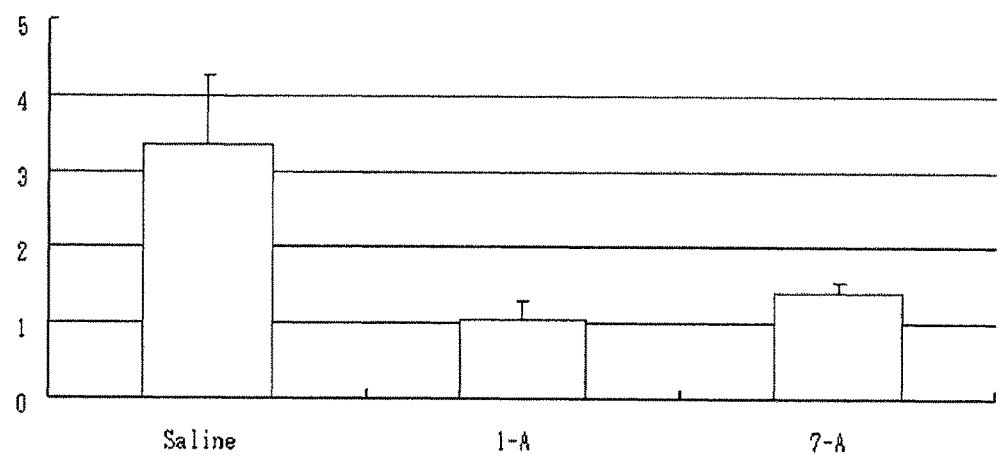
[Fig.10]
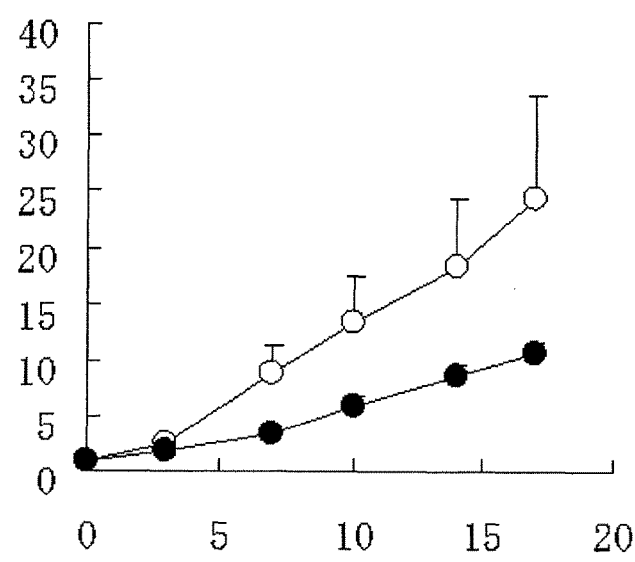

RNAI PHARMACEUTICAL COMPOSITION FOR SUPPRESSING EXPRESSION OF KRAS GENE

FIELD OF THE INVENTION

The present invention relates to a composition for suppressing the expression of a KRAS gene, a medicine comprising the composition, and the like.

BACKGROUND ART

KRAS belongs to the RAS family of proteins with a molecular weight of about 21 kDa and GTP hydrolytic activity. KRAS is found inside the cell membrane, and has a role to transmit signals into cells in response to the binding of extracellular growth factors such as Epidermal Growth Factor (EGF) with the receptors. Activating mutations can be found in KRAS, and they are found in about 20% of human cancer. The frequency of the occurrence of KRAS activating mutations is high particularly in pancreatic cancer, colon cancer, and lung cancer (see "Cancer Res", Vol. 72, p. 2457, 2012). There is a report that anti-epidermal growth factor receptor (EGFR) antibody drugs: cetuximab and panitumumab are ineffective in colon cancer patients with KRAS activating mutations (see "N Engl J Med", Vol. 360, p. 1408, 2009; "J Clin Oncol", Vol. 26, p. 374, 2008; "J Clin Oncol", Vol. 26, p. 1626, 2008). KRAS has been regarded as a desirable target of anticancer drugs, and there have been long-standing attempts to discover KRAS inhibitors by a low-molecular drug discovery approach (see "Cancer Biology & Therapy", Vol. 1, p. 599, 2002). However, there is no effective therapeutic agent for treating a cancer etc. that targets the KRAS.

As a method of suppressing the expression of a target gene, for example, a method utilizing RNA interference (hereinafter referred to as RNAi) and the like are known, and specifically, a phenomenon in which when a double-stranded RNA having a sequence identical to that of a target gene is introduced into Nematoda, the expression of the target gene is specifically suppressed has been reported (see "Nature", Vol. 391, No. 6669, pp. 806-811, 1998). Further, it has been found that even when a double-stranded RNA having a length of 21 to 23 bases is introduced into Drosophila, instead of a long double-stranded RNA, the expression of a target gene is suppressed. This is named a short interfering RNA (siRNA) (see International Publication No. WO 01/75164).

RNAi has been frequently verified also in in vivo tests. The effect of siRNA with a length of 50 base pairs or less on fetal animals (see United States Patent Application Publication No. US 2002-132788) and the effect thereof on adult mice (see International Publication No. WO 03/10180) are reported. Moreover, the effect of suppressing the expression of a specific gene has been found in each of organs that are kidney, spleen, lung, pancreas, and liver when siRNA is intravenously administered to a fetal mouse (see "Nature Genetics", Vol. 32, No. 1, pp. 107-108, 2002). Furthermore, it has been reported that also when siRNA is directly administered to brain cells, the expression of a specific gene is suppressed (see "Nature Biotechnology", Vol. 20, No. 10, pp. 1006-1010, 2002).

KRAS siRNA is described in, for example, Patent Document 1, Patent Document 2, etc.

Medicines containing an siRNA are described in, for example, Patent Document 3, Patent Document 4, Patent Document 5, etc.

Patent Document 3 discloses medicines containing an siRNA and, for example, 1,2-dilinoleyloxy-N,N-dimethylaminopropane (DLinDMA) etc. DLinDMA etc. are characterized in that for the purpose of developing more flexible cationic lipids, thereby increasing the membrane fluidity of a liposome or the like, the higher alkyl groups of N-(2,3-di-(9-(Z)-octadecenoyloxy))-propan-1-yl-N,N,N-trimethyl-ammonium chloride (DOTAP) and N-[1-(2,3-dioleyloxy)propyl]-N,N,N-trimethylammonium chloride (DOTMA) that are structurally analogous cationic lipids thereto are replaced by higher alkyl groups containing at least two sites of unsaturation. In addition, Patent Document 4 discloses medicines containing an siRNA and, for example, 2,2-dilinoleyl-4-dimethylaminomethyl-[1,3]-dioxolane (DLin-K-DMA) etc.

In addition, Patent Document 5 discloses, for example, trans-3,4-bis(((Z)-octadeca-9-enoyloxy)methyl)pyrrolidine (Compound I-3) etc.

CITATION LIST

Patent Documents

Patent Document 1: WO2008/109516
Patent Document 2: WO2010/115206
Patent Document 3: WO2005/121348
Patent Document 4: WO2009/086558
Patent Document 5: WO2011/136368

SUMMARY OF THE INVENTION

Problems to be Solved by the Invention

An object of the present invention is to provide a composition for suppressing the expression of a KRAS gene, a medicine comprising the composition, and the like.

Means for Solving the Problems

The present invention relates to the following (1) to (23).
(1) A composition comprising a lipid particle containing, as a drug, a double-stranded nucleic acid having a sense strand and an antisense strand, the sense strand and the antisense strand having at least 25 base pairs, and the antisense strand having a sequence of bases complementary to the sequence of at least 19 continuous bases of any one KRAS gene's mRNA of sequence Nos. 1 to 3 and having a length of 35 nucleotides at maximum; and
a cationic lipid represented by the following formula (I):

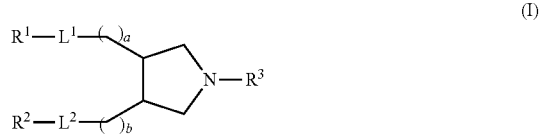

(I)

wherein
$R^1$ and $R^2$, which are the same or different, are each linear or branched alkyl, alkenyl or alkynyl having a carbon number of from 12 to 24;
$L^1$ and $L^2$, which are the same or different, each —CO—O— or —O—CO—;
a and b, which are the same or different, are each 1 to 3; and

3

R³ is a hydrogen atom, alkyl having a carbon number of from 1 to 6, or alkenyl having a carbon number of from 3 to 6.

(2) The composition as set forth above in (1), wherein the lipid particle is a lipid particle further containing a cationic lipid represented by the following formula (II):

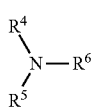

(II)

wherein

R⁴ and R⁵, which are the same or different, are each linear or branched alkyl, alkenyl or alkynyl having a carbon number of from 12 to 24; and R⁶ is a hydrogen atom, alkyl having a carbon number of from 1 to 6, alkenyl having a carbon number of from 3 to 6, pyrrolidin-3-yl, piperidin-3-yl, piperidin-4-yl, or alkyl having a carbon number of from 1 to 6 or alkenyl having a carbon number of from 3 to 6, each substituted with the same or different one to three of amino, monoalkylamino, dialkylamino, hydroxy, alkoxy, carbamoyl, monoalkylcarbamoyl, dialkylcarbamoyl, pyrrolidinyl, piperidyl, and morpholinyl.

(3) The composition as set forth above in (2), wherein R⁴ and R⁵ are identically dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, or 3,7,11,15-tetramethylhexadec-2-enyl.

(4) The composition as set forth above in (2), wherein R⁴ and R⁵ are identically tetradecyl, hexadecyl, (Z)-hexadec-9-enyl, (Z)-octadec-6-enyl, (Z)-octadec-9-enyl, (9Z,12Z)-octadeca-9,12-dienyl, (Z)-icos-11-enyl, or (11Z,14Z)-icosa-11,14-dienyl.

(5) The composition as set forth above in (3) or (4), wherein R⁶ is a hydrogen atom, methyl, pyrrolidin-3-yl, piperidin-3-yl, piperidin-4-yl, or alkyl having a carbon number of from 1 to 6 or alkenyl having a carbon number of from 3 to 6, each substituted with the same or different one to three of amino, monoalkylamino, dialkylamino, hydroxy, alkoxy, carbamoyl, monoalkylcarbamoyl, dialkylcarbamoyl, pyrrolidinyl, piperidyl, and morpholinyl.

(6) The composition as set forth above in any one of (1) to (5), wherein R³ is a hydrogen atom or methyl.

(7) The composition as set forth above in any one of (1) to (6), wherein L¹ and L² are each —O—CO—; and R¹ and R² are identically dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, or 3,7,11,15-tetramethylhexadec-2-enyl.

(8) The composition as set forth above in any one of (1) to (6), wherein L¹ and L² are each —CO—O—; and R¹ and R² are identically tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-heptadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl, or 2,6,10,14-tetramethylpentadec-1-enyl.

(9) The composition as set forth above in any one of (1) to (8), containing, as the drug, a double-stranded nucleic acid having a sense strand and an antisense strand, each being sequence Nos. 4 and 5, 6 and 7, 8 and 9, 4 and 10, or 4 and 11.

(10) The composition as set forth above in any one of (1) to (9), wherein the cationic lipid forms a complex together with the double-stranded nucleic acid, or forms a complex between a combination of the cationic lipid with a neutral lipid and/or a polymer and the double-stranded nucleic acid.

(11) The composition as set forth above in any one of (1) to (9), wherein the cationic lipid forms a complex together with the double-stranded nucleic acid, or forms a complex between a combination of the cationic lipid with a neutral lipid and/or a polymer and the double-stranded nucleic acid, and the lipid particle is constituted of the complex and a lipid membrane for encapsulating the complex.

(12) A method for suppressing the expression of a RAS gene comprising, introducing the double-stranded nucleic acid into a cell by using the composition as set forth above in any one of (1) to (11).

(13) The method as set forth above in (12), wherein the cell is a cell present in tumor of a mammal.

(14) The method as set forth above in (12), wherein the cell is a cell present in a large intestine or a pancreas of a mammal.

(15) The method as set forth above in any one of (12) to (14), wherein the method of the introduction into a cell is a method of introduction into a cell by intravenous administration.

(16) A method for treating a RAS-associated disease comprising administering the composition as set forth above in any one of (1) to (11) to a mammal.

(17) The method as set forth above in (16), wherein the method of the administration is intravenous administration.

(18) A method for treating a cancer comprising administering the composition as set forth above in any one of (1) to (11) to a mammal.

(19) The method as set forth above in (18), wherein the method of the administration is intravenous administration.

(20) A medicine comprising the composition as set forth above in any one of (1) to (11), for the use in treating a RAS-associated disease.

(21) The medicine as set forth above in (20), which is for intravenous administration.

(22) A therapeutic agent for cancer comprising the composition as set forth above in any one of (1) to (11).

(23) The therapeutic agent for cancer as set forth above in (22), which is for intravenous administration.

Effects of the Invention

A RAS-associated disease can be treated by, for example, administrating the composition of the present invention to a mammal, thereby suppressing the expression of a KRAS gene in a living body.

BRIEF DESCRIPTION OF THE DRAWINGS

FIG. 1 shows an amount of KRAS mRNA in tumor 48 hours after the administration of the preparations 1-A to C obtained in Example 1 to MIA PaCa-2 xenograft mice in an amount equivalent to 10 mg/kg siRNA. The ordinate represents a relative value of an amount of KRAS mRNA while defining that of a saline-administered group as 1.

FIG. 2 shows a transition of a relative value of a tumor volume when the preparations 1-A to C obtained in Example 1 were administered on Day 0 and Day 7 to MIA PaCa-2 xenograft mice in an amount equivalent to 10 mg/kg siRNA. The ordinate represents a relative value of a tumor volume while defining that on Day 0 as 1. The abscissa represents a number of elapsed days after the start of experiment. Meanings of white and black circles on the graph are as the saline-administered groups and the preparation-administered groups, respectively.

FIG. 3 shows an amount of anti-PEG antibody in blood 7 days after the administration of the preparations 1-A to C obtained in Example 1 to BALE/c mice in an amount equivalent to 10 mg/kg siRNA. The ordinate represents a production amount of anti-PEG antibody.

FIG. 4 shows an amount of KRAS mRNA in tumor 48 hours after the administration of the preparation 2-A, D, or E obtained in Example 2 to MIAPaCa-2 xenograft mice each in an amount equivalent to 1, 3, or 10 mg/kg siRNA. The ordinate represents a relative value of an amount of KRAS mRNA while defining that of a saline-administered group as 1. The abscissa represents a dose of each preparation.

FIG. 5 shows a relative value of a tumor volume 7 days after the administration of the preparation 2-A, D, or E obtained in Example 2 to MIAPaCa-2 xenograft mice each in an amount equivalent to 1, 3, or 10 mg/kg siRNA. The ordinate represents a relative value of a tumor volume while defining that on Day 0 as 1. The abscissa represents a dose of each preparation.

FIG. 6 shows a relative value of a tumor volume 7 days after the administration of the preparations 1-A and 2-A obtained in Examples 1 and 2, respectively, to MIAPaCa-2 xenograft mice in an amount equivalent to 2.5 mg/kg siRNA. The ordinate represents a relative value of a tumor volume while defining that on Day 0 as 1.

FIG. 7 shows a relative value of a tumor volume 7 days after the administration of the preparations 1-A, 3-A and 4-A obtained in Examples 1, 3 and 4, respectively, to MIAPaCa-2 xenograft mice in an amount equivalent to 2.5 mg/kg siRNA. The ordinate represents a relative value of a tumor volume while defining that on Day 0 as 1.

FIG. 8 shows a relative value of a tumor volume 7 days after the administration of the preparations 1-A, 5-A, and 6-A obtained in Examples 1, 5, and 6, respectively, to MIAPaCa-2 xenograft mice in an amount equivalent to 2.5 mg/kg siRNA. The ordinate represents a relative value of a tumor volume while defining that on Day 0 as 1.

FIG. 9 shows a relative value of a tumor volume 7 days after the administration of the preparations 1-A and 7-A obtained in Examples 1 and 7, respectively, to MIAPaCa-2 xenograft mice in an amount equivalent to 5 mg/kg siRNA. The ordinate represents a relative value of a tumor volume while defining that on Day 0 as 1.

FIG. 10 shows a transition of a relative value of a tumor volume when the preparation 1-A obtained in Example 1 was administered on Day 0 and Day 7 to HCT116 xenograft mice in an amount equivalent to 10 mg/kg siRNA. The ordinate represents a relative value of a tumor volume while defining that on Day 0 as 1. The abscissa represents a number of elapsed days after the start of experiment. Meanings of white and black circles on the graph are as the saline-administered group and the preparation-administered group.

MODES FOR CARRYING OUT THE INVENTION

The present invention provides a composition comprising a lipid particle containing,
as a drug, a double-stranded nucleic acid having an ability to reduce or stop the expression of a KRAS gene; and
a cationic lipid.

In addition, the present invention also provides a method for treating a RAS-associated disease by administrating the composition to a mammal, thereby suppressing the expression of a KRAS gene in a living body.

Furthermore, the present invention provides a method for treating or preventing an exuberant malady or disease (for example, leukemia, melanoma, blastoma, cancer, tumor, adenoma, etc.) or at least one angiogenic disease associated with an inappropriate expression of a RAS gene.

The lipid particle in the composition of the present invention contains a cationic lipid represented by the following formula (I):

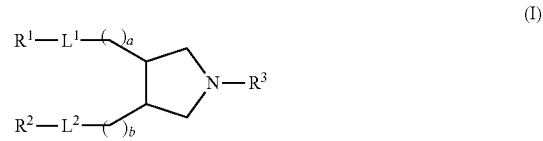

wherein
$R^1$ and $R^2$, which are the same or different, are each linear or branched alkyl, alkenyl or alkynyl having a carbon number of from 12 to 24;
$L^1$ and $L^2$, which are the same or different, are each —CO—O— or —O—CO—;
a and b, which are the same or different, are each 1 to 3; and
$R^3$ is a hydrogen atom, alkyl having a carbon number of from 1 to 6, or alkenyl having a carbon number of from 3 to 6.

The compound represented by the formula (I) will be hereinafter also referred to as "compound (I)". The same is also applicable to compounds designated with other numbers.

In addition, the lipid particle in the composition of the present invention is a lipid particle containing Compound (I) and a cationic lipid represented by the following formula (II):

wherein
$R^4$ and $R^5$, which are the same or different, are each linear or branched alkyl, alkenyl or alkynyl having a carbon number of from 12 to 24; and
$R^6$ is a hydrogen atom, alkyl having a carbon number of from 1 to 6, alkenyl having a carbon number of from 3 to 6, pyrrolidin-3-yl, piperidin-3-yl, piperidin-4-yl, or alkyl having a carbon number of from 1 to 6 or alkenyl having a carbon number of from 3 to 6, each substituted with the same or different one to three of amino, monoalkylamino, dialkylamino, hydroxy, alkoxy, carbamoyl, monoalkylcarbamoyl, dialkylcarbamoyl, pyrrolidinyl, piperidyl, and morpholinyl.

In the definition of each group of the formula (I), examples of the linear or branched alkyl having a carbon number of from 12 to 24 include dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl, and tetracosyl.

In the definition of each group of the formula (I), the linear or branched alkenyl having a carbon number of from 12 to 24 may be linear or branched alkenyl having a carbon number of from 12 to 24 and having from 1 to 3 double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-heptadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl, and 3,7,11,15-tetramethylhexadec-2-enyl. Of these, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl, (9Z,12Z)-octadeca-9,12-dienyl, and the like are preferable.

In the definition of each group of the formula (I), the linear or branched alkynyl having a carbon number of from 12 to 24 may be linear or branched alkynyl having a carbon number of from 12 to 24 and having from 1 to 3 triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl, and octadec-9-ynyl.

Incidentally, in Compound (I), it is preferable that $R^1$ and $R^2$ are the same, and are linear or branched alkyl, alkenyl or alkynyl having a carbon number of from 12 to 24. In addition, it is more preferable that each of $R^1$ and $R^2$ is linear or branched alkyl or alkenyl having a carbon number of from 12 to 24; and still more preferable that each of $R^1$ and $R^2$ is linear alkenyl having a carbon number of from 12 to 24.

In the definition of each group of the formula (II), examples of the linear or branched alkyl having a carbon number of from 12 to 24 include dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl, and tetracosyl.

In the definition of each group of the formula (II), the linear or branched alkenyl having a carbon number of from 12 to 24 may be linear or branched alkenyl having a carbon number of from 12 to 24 and having from 1 to 3 double bonds. Examples thereof include (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, and 3,7,11,15-tetramethylhexadec-2-enyl. Of these, (Z)-hexadec-9-enyl, (Z)-octadec-6-enyl, (Z)-octadec-9-enyl, (9Z,12Z)-octadeca-9,12-dienyl, (Z)-icos-11-enyl, (11Z,14Z)-icosa-11,14-dienyl, and the like are preferable.

In the definition of each group of the formula (II), the linear or branched alkynyl having a carbon number of from 12 to 24 may be linear or branched alkynyl having a carbon number of from 12 to 24 and having from 1 to 3 triple bonds. Examples thereof include dodec-11-ynyl, tetradec-6-ynyl, hexadec-7-ynyl, hexadeca-5,7-diynyl, and octadec-9-ynyl.

Incidentally, in the formula (II), it is preferable that $R^4$ and $R^5$ are the same, and are linear or branched alkyl, alkenyl or alkynyl having a carbon number of from 12 to 24. In addition, it is more preferable that each of $R^4$ and $R^5$ is linear or branched alkyl or alkenyl having a carbon number of from 12 to 24; and still more preferable that each of $R^4$ and $R^5$ is linear alkenyl having a carbon number of from 12 to 24.

In the definition of each group of the formula (I) and the formula (II), examples of the alkyl having a carbon number of from to 6 include methyl, ethyl, propyl, isopropyl, cyclopropyl, butyl, isobutyl, sec-butyl, tert-butyl, cyclobutyl, cyclopropylmethyl, pentyl, isopentyl, sec-pentyl, neopentyl, tert-pentyl, cyclopentyl, hexyl, and cyclohexyl. Of these, methyl, ethyl, propyl, isopropyl, butyl, isobutyl, sec-butyl, tert-butyl, pentyl, isopentyl, sec-pentyl, tert-pentyl, neopentyl, hexyl, and the like are preferable, with methyl, ethyl, propyl, and the like being more preferable.

Examples of the alkenyl having a carbon number of from 3 to 6 include allyl, 1-propenyl, butenyl, pentenyl, and hexenyl. Of these, allyl and the like are preferable.

The alkyl moiety in the substituted alkyl having a carbon number of from 1 to 6 and the alkenyl moiety in the substituted alkenyl having a carbon number of from 3 to 6 are synonymous with the alkyl having a carbon number of from 1 to 6 and the alkenyl having a carbon number of from 3 to 6 as described above, respectively.

In Compounds (I) and (II), a hydrogen ion may coordinate to a lone pair on the nitrogen atom in the structure; the nitrogen atom to which a hydrogen ion coordinates may form a salt together with a pharmaceutically acceptable anion; and each of Compounds (I) and (II) includes a compound in which a hydrogen ion coordinates to a lone pair on the nitrogen atom.

Examples of the pharmaceutically acceptable anion include inorganic ions such as a chloride ion, a bromide ion, a nitrate ion, a sulfate ion, and a phosphate ion; and organic acid ions such as an acetate ion, an oxalate ion, a maleate ion, a fumarate ion, a citrate ion, a benzoate ion, and a methanesulfonate ion.

In the definition of each group of the formula (II), each of pyrrolidin-3-yl, piperidin-3-yl and piperidin-4-yl includes the one in which the hydrogen atom bonded on the nitrogen atom in the ring is converted into methyl or ethyl.

Each of the monoalkylamino and the dialkylamino may be amino which is substituted with one or the same or different two, respectively, alkyls having a carbon number of from 1 to 6 (synonymous with that as described above) or alkyls having a carbon number of from 1 to 6 (synonymous with that as described above) substituted with amino, methylamino, ethylamino, dimethylamino, diethylamino, pyrrolidinyl, piperidyl, or morpholinyl. Examples thereof include methylamino, ethylamino, propylamino, butylamino, pentylamino, hexylamino, dimethylamino, diethylamino, ethylmethylamino, methylpropylamino, butylmethylamino, methylpentylamino, hexylmethylamino, aminoethylamino, aminopropylamino, (aminoethyl)methylamino, and bis(aminoethyl)amino. Of these, methylamino, ethylamino, dimethylamino, diethylamino, aminopropylamino, and bis(aminoethyl)amino, and the like are preferable.

In Compound (II), the amino, the monoalkylamino, and the dialkylamino may form an ammonio, a monoalkylammonio, and a dialkylammonio, respectively through coordination of a hydrogen ion to a lone pair on the nitrogen atom. The amino, the monoalkylamino, and the dialkylamino include the ammonio, the monoalkylammonio, and the dialkylammonio, respectively. In this case, each of the ammonio, the monoalkylammonio, and the dialkylammonio in which a hydrogen ion coordinates to a lone pair on the nitrogen atom of the amino, the monoalkylamino, and the dialkylamino, respectively may form a salt together with a pharmaceutically acceptable anion (synonymous with that as described above).

The alkoxy may be hydroxy which is substituted with alkyl having a carbon number of from 1 to 6 (synonymous with that as described above) or alkyl having a carbon number of from 1 to 6 (synonymous with that as described above) substituted with amino, methylamino, ethylamino, dimethylamino, diethylamino, pyrrolidinyl, piperidyl, or morpholinyl. Examples thereof include methoxy, ethoxy, propyloxy, butyloxy, pentyloxy, hexyloxy, aminoethoxy, and methylaminoethoxy. Of these, methoxy, ethoxy, aminoethoxy, methylaminoethoxy, and the like are preferable.

Each of the monoalkylcarbamoyl and the dialkylcarbamoyl may be carbamoyl which is substituted with one or the same or different two, respectively, alkyls having a carbon number of from 1 to 6 (synonymous with that as described above) or alkyls having a carbon number of from 1 to 6 (synonymous with that as described above) substituted with amino, methylamino, ethylamino, dimethylamino, diethylamino, pyrrolidinyl, piperidyl, or morpholinyl. Examples thereof include methylcarbamoyl, ethylcarbamoyl, propylcarbamoyl, butylcarbamoyl, pentylcarbamoyl, hexylcarbamoyl, dimethylcarbamoyl, diethylcarbamoyl, ethylmethylcarbamoyl, methylpropylcarbamoyl, butylmethylcarbamoyl, methylpentylcarbamoyl, hexylmethylcarbamoyl, aminoethylcarbamoyl, aminopropylcarbamoyl, (aminoethyl)methylcarbamoyl, and bis(aminoethyl)carbamoyl. Of these, methylcarbamoyl, ethylcarbamoyl, dimethylcarbamoyl, and the like are preferable.

In Compound (I), when $L^1$ and $L^2$ are each —O—CO—, then $R^1$ and $R^2$, which are the same or different, are each more preferably dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, or 3,7,11,15-tetramethylhexadec-2-enyl; and still more preferably tetradecyl, hexadecyl, octadecyl, (Z)-hexadec-9-enyl, (Z)-octadec-6-enyl, (Z)-octadec-9-enyl, (9Z,12Z)-octadeca-9,12-dienyl, (Z)-icos-11-enyl, or (11Z,14Z)-icosa-11,14-dienyl. Incidentally, in all of the cases, it is more preferable that $R^1$ and $R^2$ are the same as each other.

In addition, when $L^1$ and $L^2$ are each —CO—O—, then $R^1$ and $R^2$, which are the same or different, are each more preferably tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-heptadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl, or 2,6,10,14-tetramethylpentadec-1-enyl; and still more preferably tridecyl, pentadecyl, heptadecyl, (Z)-pentadec-8-enyl, (Z)-heptadec-5-enyl, (Z)-heptadec-8-enyl, (8Z,11Z)-heptadeca-8,11-dienyl, (Z)-nonadec-10-enyl, or (10Z,13Z)-nonadeca-10,13-dienyl. Incidentally, in all of the cases, it is preferable that $R^1$ and $R^2$ are the same as each other.

In addition, it is more preferable that a and b are 1 at the same time.

In addition, it is also one of preferred embodiments of the present invention that not only a and b are 1 at the same time, but $L^1$ and $L^2$ are each —CO—O—. In that case, $R^1$ and $R^2$, which are the same or different, are each more preferably (Z)-heptadec-8-enyl or (8Z,11Z)-heptadeca-8,11-dienyl, and most preferably these are identically (Z)-heptadec-8-enyl or (8Z,11Z)-heptadeca-8,11-dienyl.

In addition, $R^3$ is more preferably a hydrogen atom or methyl.

In addition, it is also one of more preferred embodiments of the present invention that a and b are each 1, $L^1$ and $L^2$ are identically —CO—O— or —O—CO—, and preferably —CO—O—, and $R^3$ is methyl. $R^1$ and $R^2$, which are the same or different, are more preferably (Z)-heptadec-8-enyl or (8Z,11Z)-heptadeca-8,11-dienyl, and most preferably these are identically (Z)-heptadec-8-enyl or (8Z,11Z)-heptadeca-8,11-dienyl.

Incidentally, it is also one of preferred embodiments of the present invention that when $R^3$ is a hydrogen atom, then $L^1$ and $L^2$ are identically —CO—O— or —O—CO—, and preferably –CO—O—. $R^1$ and $R^2$, which are the same or different, are more preferably (Z)-heptadec-5-enyl or (Z)-heptadec-8-enyl, and most preferably these are identically (Z)-heptadec-5-enyl or (Z)-heptadec-8-enyl.

In Compound (II), $R^4$ and $R^5$, which are the same or different, are each preferably tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, or (11Z,14Z)-icosa-11,14-dienyl; more preferably (Z)-octadec-9-enylor, or (9Z,12Z)-octadeca-9,12-dienyl; and most preferably these are identically (Z)-octadec-9-enyl, or (9Z,12Z)-octadeca-9,12-dienyl.

In addition, $R^6$ is preferably a hydrogen atom, methyl, pyrrolidin-3-yl, piperidin-3-yl, piperidin-4-yl, or alkyl having a carbon number of from 1 to 6 or alkenyl having a carbon number of from 3 to 6, each substituted with the same or different one to three of amino, monoalkylamino, dialkylamino, hydroxy, alkoxy, carbamoyl, monoalkylcarbamoyl, dialkylcarbamoyl, pyrrolidinyl, piperidyl, or morpholinyl; more preferably a hydrogen atom, methyl, or alkyl having a carbon number of from 1 to 6 or alkenyl having a carbon number of from 3 to 6, each substituted with one amino, hydroxy, or carbamoyl; and most preferably a hydrogen atom, methyl or the like.

In addition, it is also one of more preferred embodiments of the present invention that $R^6$ is a hydrogen atom. In that case, $R^4$ and $R^5$, which are the same or different, are each more preferably tetradecyl, hexadecyl, (Z)-hexadec-9-enyl, (Z)-octadec-6-enyl, (Z)-octadec-9-enyl, (9Z,12Z)-octadeca-9,12-dienyl, (Z)-icos-11-enyl, or (11Z,14Z)-icosa-11,14-dienyl, and most preferably these are identically (Z)-hexadec-9-enyl, (Z)-octadec-9-enyl, or (9Z,12Z)-octadeca-9,12-dienyl.

In addition, it is also one of more preferred embodiments of the present invention that $R^6$ is methyl. In that case, $R^4$ and $R^5$, which are the same or different, are each more preferably tetradecyl, hexadecyl, (Z)-hexadec-9-enyl, (Z)-octadec-6-enyl, (Z)-octadec-9-enyl, (9Z,12Z)-octadeca-9,12-dienyl, (Z)-icos-11-enyl, or (11Z,14Z)-icosa-11,14-dienyl, and most preferably these are identically (Z)-hexadec-9-enyl, (Z)-octadec-9-enyl, or (9Z,12Z)-octadeca-9,12-dienyl.

Compound (I) can be obtained in the same method as the production method described in International Publication No. WO2011/136368. Incidentally, in the case where the defined group or groups change under a condition of the production method or are impertinent for carrying out the production method, the target compound can be produced by adopting an introduction and removal method of a protective group which is commonly adopted in the synthetic organic chemistry [for example, a method described in *Protective Groups in Organic Synthesis, third edition*, written by T. W. Greene, John Wiley & Sons Inc. (1999), etc.] In addition, if desired, the order of reaction steps such as introduction of a substituent can be altered, too.

Next, production methods of Compound (II) are described. Incidentally, in the following production methods, in the case where the defined group or groups change under a condition of the production method or are impertinent for carrying out the production method, the target compound can be produced by adopting an introduction and removal method of a protective group which is commonly adopted in the synthetic organic chemistry [for example, a method described in *Protective Groups in Organic Synthesis, third edition*, written by T. W. Greene, John Wiley & Sons Inc. (1999), etc.] In addition, if desired, the order of reaction steps such as introduction of a substituent can be altered, too.

Production Method 1

Compound (II) can be produced by the following method.

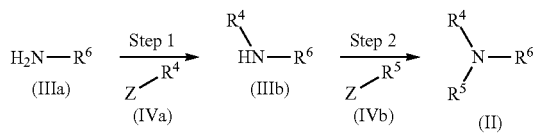

In the foregoing formulae, $R^4$, $R^5$, and $R^6$ are synonymous with those as described above, respectively; and Z represents a leaving group such as a chlorine atom, a bromine atom, an iodine atom, trifluoromethanesulfonyloxy, methanesulfonyloxy, benzenesulfonyloxy, and p-toluenesulfonyloxy.

Steps 1 and 2

Compound (IIIb) can be produced by reacting Compound (IIIa) and Compound (IVa) in the absence or presence of a solvent and optionally in the presence of bases in an amount of preferably from 1 to 10 equivalents at a temperature between room temperature and 200° C. for from 5 minutes to 100 hours. Further, Compound (II) can be produced by reacting Compound (IIIb) and Compound (IVb) in the absence or presence of a solvent and optionally in the presence of bases in an amount of preferably from 1 to 10 equivalents at a temperature between room temperature and 200° C. for from 5 minutes to 100 hours.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, pyridine, and water. These solvents are used solely or in combination.

Examples of the base include potassium carbonate, potassium hydroxide, sodium hydroxide, sodium methoxide, potassium tert-butoxide, triethylamine, diisopropylethylamine, N-methylmorpholine, pyridine, and 1,8-diazabicyclo[5.4.0]-7-undecene (DBU).

Compound (IIIa) can be obtained as a commercially available product or by a known method (for example, Dai 5-han, *Jikken Kagaku Kouza* (5th edition, Courses in Experimental Chemistry) 14, "Synthesis of Organic Compounds II", 5th edition, p. 351, Maruzen (2005)) or a method similar thereto.

Each of Compound (IVa) and Compound (IVb) can be obtained as a commercially available product or by a known method (for example, Dai 5-han, *Jikken Kagaku Kouza* (5th edition, Courses in Experimental Chemistry) 13, "Synthesis of Organic Compounds I", 5th edition, p. 374, Maruzen (2005)) or a method similar thereto.

Compound (IIa) in the case where $R^4$ and $R^5$ are identical can be obtained using 2 equivalents or more of Compound (IVa) in Step 1.

Production Method 2

In Compound (II), Compound (IIb) in which $R^6$ is —CHR$^A$R$^B$ (in the formula, R$^A$ and R$^B$, which are the same or different, are each a hydrogen atom, alkyl having a carbon number of from 1 to 5, alkenyl having a carbon number of from 2 to 5, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 5 or alkenyl having a carbon number of from 2 to 5, each substituted with the same or different one to three of amino, monoalkylamino, dialkylamino, hydroxy, alkoxy, carbamoyl, monoalkylcarbamoyl, dialkylcarbamoyl, pyrrolidinyl, piperidyl, or morpholinyl, or taken together with the adjacent carbon atom to form pyrrolidin-3-yl, piperidin-3-yl, or piperidin-4-yl; a total sum of the carbon number of each of the alkyl, the alkyl moiety of the substituted alkyl, the alkenyl, and the alkenyl moiety of the substituted alkenyl in R$^A$ and R$^B$ is from 1 to 5, except the case where R$^A$ and R$^B$ are each a hydrogen atom; in the case where either R$^A$ or R$^B$ is pyrrolidin-2-yl, pyrrolidin-3-yl, piperidin-2-yl, piperidin-3-yl, piperidin-4-yl, morpholin-2-yl, or morpholin-3-yl, the other R$^A$ or R$^B$ is a hydrogen atom, alkyl having a carbon number of from 1 to 5, alkenyl having a carbon number of from 2 to 5, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 5 or alkenyl having a carbon number of from 2 to 5, each substituted with the same or different one or two of amino, monoalkylamino, dialkylamino, hydroxy, alkoxy, carbamoyl, monoalkylcarbamoyl, dialkylcarbamoyl, pyrrolidinyl, piperidyl, or morpholinyl; and in the case where R$^A$ and R$^B$ are each substituted alkyl or alkenyl, a total sum of the number of the substituents is 2 or 3); can be produced in the following method, too.

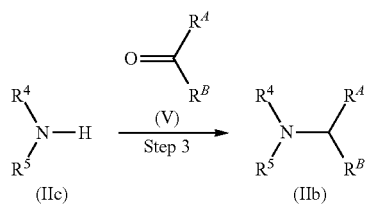

In the foregoing formulae, $R^4$, $R^5$, R$^A$, and R$^B$ are synonymous with those as described above, respectively.

Step 3

Compound (IIb) can be produced by allowing Compound (IIc) in which $R^6$ in Compound (II) is a hydrogen atom to react with Compound (V) in an amount of preferably from 1 to 10 equivalents in a solvent in the presence of a reducing agent in an amount of preferably from 1 equivalent to a large excess and optionally an acid in an amount of preferably from 1 to 10 equivalents at a temperature between −20° C. and 150° C. for from 5 minutes to 72 hours.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, and water. These solvents are used solely or in combination.

Examples of the reducing agent include sodium triacetoxyborohydride and sodium cyanoborohydride.

Examples of the acid include hydrochloric acid and acetic acid.

Compound (V) can be obtained as a commercially available product or by a known method (for example, Dai 5-han, *Jikken Kagaku Kouza* (5th edition, Courses in Experimental Chemistry) 15, "Synthesis of Organic Compounds III", 5th edition, p. 1, Maruzen (2005); and Dai 5-han, *Jikken Kagaku Kouza* (5th edition, Courses in Experimental Chemistry) 15, "Synthesis of Organic Compounds III", 5th edition, p. 153, Maruzen (2005)) or a method similar thereto.

Production Method 3

In Compound (II), Compound (IId) in which $R^6$ is $-CH_2-C(OH)R^C R^D$ (in the formula, $R^C$ and $R^D$, which are the same or different, are each a hydrogen atom, alkyl having a carbon number of from 1 to 4, alkenyl having a carbon number of from 2 to 4, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 4 or alkenyl having a carbon number of from 2 to 4, each substituted with the same or different one or two of amino, monoalkylamino, dialkylamino, hydroxy, alkoxy, carbamoyl, monoalkylcarbamoyl, dialkylcarbamoyl, pyrrolidinyl, piperidyl, or morpholinyl; a total sum of the carbon number of each of the alkyl, the alkyl moiety of the substituted alkyl, the alkenyl, and the alkenyl moiety of the substituted alkenyl in $R^C$ and $R^D$ is from 1 to 4 except the case where $R^C$ and $R^D$ are each a hydrogen atom; in the case where either $R^C$ or $R^D$ is pyrrolidin-2-yl, pyrrolidin-3-yl, piperidin-2-yl, piperidin-3-yl, piperidin-4-yl, morpholin-2-yl, or morpholin-3-yl, the other $R^C$ or $R^D$ is a hydrogen atom, alkyl having a carbon number of from 1 to 4, alkenyl having a carbon number of from 2 to 4, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 4 or alkenyl having a carbon number of from 2 to 4, each substituted with one amino, monoalkylamino, dialkylamino, hydroxy, alkoxy, carbamoyl, monoalkylcarbamoyl, dialkylcarbamoyl, pyrrolidinyl, piperidyl, or morpholinyl; and in the case where $R^C$ and $R^D$ are each a substituted alkyl or alkenyl, a total sum of the number of the substituents is 2) can be produced in the following method, too.

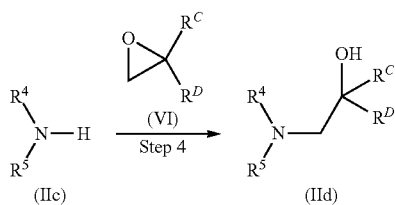

In the foregoing formulae, $R^4$, $R^5$, $R^C$, and $R^D$ are synonymous with those as described above, respectively.

Step 4

Compound (IId) can be produced by reacting Compound (IIc) and Compound (VI) in the absence or presence of a solvent at a temperature between 0° C. and 230° C. for from 5 minutes to 100 hours.

Examples of the solvent include methanol, ethanol, 1-propanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, and dimethyl sulfoxide. These solvents are used solely or in combination.

Compound (VI) can be obtained as a commercially available product or by a known method (for example, Dai 5-han, *Jikken Kagaku Kouza* (5th edition, Courses in Experimental Chemistry) 17, "Synthesis of Organic Compounds V", 5th edition, p. 186, Maruzen (2005)) or a method similar thereto.

Conversion of the functional groups contained in $R^4$, $R^5$, and $R^6$ in Compound (II) can also be carried out by a known method [for example, a method described in *Comprehensive Organic Transformations 2nd edition*, written by R. C. Larock, Vch Verlagsgesellschaft Mbh (1999), etc.] or a method similar thereto.

The intermediate and the target compound in each of the foregoing production methods can be isolated and purified by means of a separation and purification method which is commonly adopted in the synthetic organic chemistry, for example, filtration, extraction, washing, drying, concentration, recrystallization, a variety of chromatography, etc. In addition, in the intermediate, it is also possible to subject it to the subsequent reaction without being particularly purified.

In Compounds (I) and (II), there may exist compounds in which stereoisomer such as geometrical isomers and optical isomers, tautomers, and the like. Compounds (I) and (II) include all of possible isomers and mixtures thereof inclusive of the foregoing stereoisomers and tautomers.

A part or all of the respective atoms in Compounds (I) and (II) may be substituted with a corresponding isotope atom. Compounds (I) and (II) include compounds in which a part or all of the respective atoms thereof are substituted with those isotope atoms. For example, a part or all of hydrogen atoms in each of Compounds (I) and (II) may be a hydrogen atom having an atomic weight of 2 (heavy hydrogen atom).

The compound in which a part or all of the respective atoms in each of Compounds (I) and (II) are substituted with a corresponding isotope atom can be produced using a commercially available building block in the same method as each of the foregoing production methods. In addition, the compound in which a part or all of hydrogen atoms in each of Compounds (I) and (II) are substituted with a heavy hydrogen atom can be synthesized adopting, for example, a method for deuterating an alcohol, a carboxylic acid, or the like using an iridium complex as a catalyst and using heavy water as a heavy hydrogen source (see *J. Am. Chem. Soc.*, Vol. 124, No. 10, 2092 (2002)); or the like.

Specific examples of Compound (I) are shown in Table 1, and specific examples of Compound (II) are shown in Table 2. However, it should not be construed that Compounds (I) and (II) in the present invention are limited thereto.

TABLE 1

| Compound No. | Strictures |
|---|---|
| I-1 | |
| I-2 | |
| I-3 | |
| I-4 | |
| I-5 | |

TABLE 2

| Compound No. | Strictures |
|---|---|
| II-1 | |
| II-2 | |
| II-3 | |

TABLE 2-continued

| Compound No. | Strictures |
|---|---|
| II-4 | (structure: two long unsaturated hydrocarbon chains attached to NH) |
| II-5 | (structure: two long unsaturated hydrocarbon chains attached to NH) |
| II-6 | (structure: two long unsaturated hydrocarbon chains attached to N—) |

In addition, the double-stranded nucleic acid as a drug to be used in the present invention is a double-stranded nucleic acid which when introduced into a mammalian cell, has ability to reduce or stop the expression of a KRAS gene, wherein the double-stranded nucleic acid is a double-stranded nucleic acid having a sense strand and an antisense strand, the sense strand and the antisense strand having at least 25 base pairs, and the antisense strand having a sequence of bases complementary to the sequence of at least 19 continuous bases of any one KRAS gene's mRNA (KRAS mRNA) of sequence Nos. 1 to 3 and having a length of 35 nucleotides at maximum.

The double-stranded nucleic acid may be any double-stranded molecule so far as it is a molecule obtained through polymerization of nucleotides and/or molecules having an equal function to the nucleotide. Examples thereof include RNA that is a polymer of ribonucleotides; DNA that is a polymer of deoxyribonucleotides; a chimera nucleic acid composed of RNA and DNA; and a nucleotide polymer in which at least one nucleotide in these nucleic acids is substituted with a molecule having an equal function to the nucleotide. In addition, a derivative containing at least one molecule obtained through polymerization of nucleotides and/or molecules having an equal function to the nucleotide as a building block is also included in the double-stranded nucleic acid of the present invention. In addition, Examples thereof include a peptide nucleic acid (PNA) [Acc. Chem. Res., 32, 624 (1999)], an oxy-peptide nucleic acid (OPNA) [J. Am. Chem. Soc., 123, 4653 (2001)], a peptide ribonucleic acid (PRNA)[J. Am. Chem. Soc., 122, 6900 (2000)]. Incidentally, in the present invention, uridine U in RNA and thymine T in DNA can be deemed to be replaced with each other.

Examples of the molecule having an equal function to the nucleotide include nucleotide derivatives.

The nucleotide derivative may be any molecule so far as it is a molecule obtained by applying modification to the nucleotide. For example, for the purpose of enhancing the nuclease resistance or achieving stabilization from other decomposing factor(s) as compared with naturally derived RNA or DNA, increasing the affinity to the complementary strand nucleic acid, increasing the cellular permeability, or achieving the visualization, molecules obtained by applying modification to ribonucleotide(s) or deoxyribonucleotide(s) are suitably used.

Examples of the nucleotide derivative include a sugar moiety modified nucleotide, a phosphodiester bond modified nucleotide, and a base modified nucleotide.

The sugar moiety modified nucleotide may be any nucleotide in which a part or the entirety of the chemical structure of the sugar moiety of the nucleotide is modified or substituted with an arbitrary substituent, or substituted with an arbitrary atom. Above all, a 2'-modified nucleotide is preferably used.

Examples of the modifying group in the sugar moiety modified nucleotide include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, 2'-SiH$_2$-substituted alkyl, 2'-ONO$_2$, 2'-NO$_2$, 2'-N$_3$, 2'-amino acid residue (amino acid with the hydroxyl group removed from the carboxylic acid), and 2'-O-amino acid residue (having the same definition as above), and the like. The nucleotide with the substitution by a modifying group at 2' position in the present invention also encompasses bridged nucleic acids (BNAs) having a structure in which the modifying group at 2' position is bridged to the 4' carbon atom, specifically, locked nucleic acids (LNAs) in which the oxygen atom at 2' position is bridged to the 4' carbon atom via methylene, ethylene bridged nucleic acids (ENAs) [Nucleic Acid Research, 32, e175 (2004)], and the like.

The preferred modifying group in the sugar moiety modified nucleotide include 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, and the like. More preferred examples include 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O—[2-(methoxy)ethyl], 2'-O-(3-aminopropyl), 2'-O-(2-[N,N-dimethyl]aminooxy)ethyl, 2'-O—[3-(N,N-dimethylamino)propyl], 2'-O-[2-[2-(N,N-dimethylamino)ethoxy]ethyl], 2'-O—[2-(methylamino)-2-oxoethyl], and 2'-Se-methyl. Even more preferred are 2'-O-methyl, 2'-O-ethyl, 2'-fluoro, and the like. 2'-O-methyl and 2'-O-ethyl are most preferable.

The preferred range of the modifying group in the sugar moiety modified nucleotide may also be defined based on its size. Modifying groups of a size corresponding to the size of fluoro to the size of —O-butyl are preferable, and modifying groups of a size corresponding to the size of —O-methyl to the size of —O-ethyl are more preferable.

The alkyl in the modifying group of the sugar moiety modified nucleotide is synonymous with the alkyl having a carbon number of from 1 to 6 in Compound (II).

The alkenyl in the modifying group of the sugar moiety modified nucleotide is synonymous with the alkenyl having a carbon number of from 3 to 6 in Compound (II).

Examples of the halogen in the modifying group of the sugar moiety modified nucleotide include a fluorine atom, a chlorine atom, a bromine atom, and an iodine atom.

Examples of the amino acid in the amino acid residue include aliphatic amino acids (specifically, glycine, alanine, valine, leucine, isoleucine, and the like), hydroxy amino acids (specifically, serine, threonine, and the like), acidic amino acids (specifically, aspartic acid, glutamic acid, and the like), acidic amino acid amides (specifically, asparagine, glutamine, and the like), basic amino acids (specifically, lysine, hydroxylysine, arginine, ornithine, and the like), sulfur-containing amino acids (specifically, cysteine, cystine, methionine, and the like), imino acids (specifically, proline, 4-hydroxy proline, and the like), and the like.

Examples of the substituent in the substituted alkyl and the substituted alkenyl in the sugar moiety modified nucleotide include halogen (having the same definition as above), hydroxy, sulfanyl, amino, oxo, —O-alkyl (the alkyl moiety of the —O-alkyl has the same definition as above), —S-alkyl (the alkyl moiety of the —S-alkyl has the same definition as above), —NH-alkyl (the alkyl moiety of the —NH-alkyl has the same definition as above), dialkylaminooxy (the two alkyl moieties of the dialkylaminooxy may be the same or different, and have the same definition as above), dialkylamino (the two alkyl moieties of the dialkylamino may be the same or different, and have the same definition as above), dialkylaminoalkyleneoxy (the two alkyl moieties of the dialkylaminoalkyleneoxy may be the same or different, and have the same definition as above; the alkylene means a group wherein the one hydrogen atom is removed from the above-defined alkyl), and the like, and the number of the substituent is preferably 1 to 3.

The phosphodiester bond modified nucleotide may be any nucleotide in which a part or the entirety of the chemical structure of the phosphodiester bond of the nucleotide is modified or substituted with an arbitrary substituent, or substituted with an arbitrary atom. Examples thereof include a nucleotide in which the phosphodiester bond is substituted with a phosphorothioate bond, a nucleotide in which the phosphodiester bond is substituted with a phosphorodithioate bond, a nucleotide in which the phosphodiester bond is substituted with an alkylphosphonate bond, and a nucleotide in which the phosphodiester bond is substituted with a phosphoroamidate bond.

The base modified nucleotide may be any nucleotide in which a part or the entirety of the chemical structure of the base of the nucleotide is modified or substituted with an arbitrary substituent, or substituted with an arbitrary atom. Examples thereof include a nucleotide in which an oxygen atom in the base is substituted with a sulfur atom, a nucleotide in which a hydrogen atom is substituted with an alkyl group having a carbon number of from 1 to 6, a nucleotide in which a methyl group is substituted with a hydrogen atom or an alkyl group having a carbon number of from 2 to 6, and a nucleotide in which an amino group is protected by a protective group such as an alkyl group having a carbon number of from 1 to 6 or an alkanoyl group having a carbon number of from 1 to 6.

Furthermore, examples of the nucleotide derivative include those in which other chemical substance(s) such as a lipid, a phospholipid, phenazine, folate, phenanthridine, anthraquinone, acridine, fluorescein, rhodamine, coumarin, and a pigment are added to the nucleotide or the nucleotide derivative in which at least one of the sugar moiety, the phosphodiester bond, and the base is modified. Specific examples thereof include 5'-polyamine added nucleotide derivatives, cholesterol added nucleotide derivatives, steroid added nucleotide derivatives, bile acid added nucleotide derivatives, vitamin added nucleotide derivatives, fluorescence dye Cy5 added nucleotide derivatives, fluorescence dye Cy3 added nucleotide derivatives, 6-fluorescein (FAM) added nucleotide derivatives, and biotin added nucleotide derivatives.

In addition, the nucleotide derivatives may form, together with another nucleotide or nucleotide derivative within the double-stranded nucleic acid, a crosslinked structure such as an alkylene structure, a peptide structure, a nucleotide structure, an ether structure, or an ester structure, or a structure which is a combination of at least one of these structures.

The double-stranded nucleic acid has a sufficient length such that it is subjected to processing by Dicer for the purpose of producing siRNA. In accordance with this embodiment, the double-stranded nucleic acid contains a sense strand preferably having a length between 26 and 30 nucleotides and an antisense strand which is annealed together with the sense strand under a biological condition such as a condition to be found in a cytoplasm of the cell.

In addition, the double-stranded nucleic acid may have some characteristics for increasing the processing by Dicer. In accordance with this embodiment, the double-stranded nucleic acid has a sufficient length such that it is subjected to processing by Dicer to produce siRNA and has at least one, and preferably all of the following characteristics. That is, (i) the double-stranded nucleic acid is asymmetric and has, for example, a 3'-protruding part in the antisense strand. (ii) A nucleotide derivative (synonymous with that as described above) is contained at the 3'-end of the sense strand for the purposes of Dicer binding and processing. Examples of the appropriate nucleotide derivative include nucleotides such as deoxyribonucleotides, acyclonucleotides, and analogs thereof; and sterically entangled molecules such as fluorescent molecules and analogs thereof. It is preferable that a deoxyribonucleotide is contained. In the case where a nucleotide derivative is used, a ribonucleotide in the double-stranded nucleic acid is substituted with such that the length of the double-stranded nucleic acid does not change. (iii) The sense strand contains a phosphate at the 5'-end. What the sense strand contains a phosphate at the 5'-end means that a hydroxyl group at the 5'-position of the sugar binding to the base at the 5'-end is modified with a phosphate group or a group which is converted into a phosphate group by a nucleolytic enzyme or the like in a living body.

In addition, in the double-stranded nucleic acid, it is preferable that the antisense strand or the sense strand or both of the strands have one or more 2'-O-methyl modified nucleotides.

Most preferably, the sense strand contains from 25 to 28 nucleotides, and two nucleotides at the 3'-end of the sense strand are deoxyribonucleotides. The sense strand contains a phosphate at the 5'-end. The antisense strand contains from 26 to 30 nucleotides and contains a 3'-protruding part of from 1 to 4 nucleotides. The antisense strand and the sense strand have one or more 2'-O-methyl modified nucleotides.

For example, in the case where the first base at the 5'-end of the sense strand and the antisense strand is counted as position No. 1 in terms of a 25 nucleotide sense strand and a 27 nucleotide antisense strand including a 3'-protruding part of two nucleotides, examples of the position of the 2'-O-methyl modification include a case of position Nos. 1, 2, 4, 6, 8, 12, 14, 16, 18 and 23 in the sense strand and position Nos. 1, 2, 3, 4, 11, 13, 25 and 27 in the antisense strand, a case of position Nos. 1, 2, 4, 6, 8, 12, 14, 16, 18 and 23 in the sense strand and position Nos. 1, 2, 3, 4, 11, 13, 21, 23, 25, 26 and 27 in the antisense strand, and a case of position Nos. 1, 2, 4, 6, 8, 12, 14, 16, 18 and 23 in the sense strand and position Nos. 1, 2, 3, 4, 11, 13, 15, 17, 19, 21, 23, 25, 26 and 27 in the antisense strand. In all of these cases, it is preferable that two nucleotides at the 3'-end of the sense strand are deoxyribonucleotides, and a phosphate is contained at the 5'-end of the antisense strand.

The double-stranded nucleic acid which is used in the present invention includes derivatives in which the oxygen atom or the like contained in the phosphate moiety, the ester moiety, or the like in the structure of the nucleic acid is substituted with another atom, for example, a sulfur atom etc.

In addition, in the sugar binding to the base at the 5'-end of each of the antisense strand and the sense strand, the hydroxyl group at the 5'-end may be modified with a phosphate group or the foregoing modifying group, or a group which is converted into a phosphate group or the foregoing modifying group by a nucleolytic enzyme or the like in a living body.

In addition, in the sugar binding to the base at the 3'-end of each of the antisense strand and the sense strand, the hydroxyl group at the 3'-end may be modified with a phosphate group or the foregoing modifying group, or a group which is converted into a phosphate group or the foregoing modifying group by a nucleolytic enzyme or the like in a living body.

Incidentally, the double-stranded nucleic acid which is used in the present invention can be produced adopting an already-known RNA or DNA synthesis method or RNA or DNA modification method.

The double-stranded nucleic acid can be designed to interact with a target sequence within the KRAS gene sequence.

The sequence of one strand of the double-stranded nucleic acid is complementary to the target site sequence described above. The double-stranded nucleic acid can be chemically synthesized using methods described herein.

RNA can be produced enzymatically or by partial/total organic synthesis, and modified ribonucleotides can be introduced by in vitro enzymatic or organic synthesis. In one embodiment, each strand is chemically prepared. Methods of synthesizing RNA molecules are known in the art [see Nucleic Acids Res., 1988, vol. 32, pp 936-948]. Generally, the double-stranded nucleic acid constructs can be synthesized using a solid phase oligonucleotide synthesis method (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111, 086; 6,008,400; 6,111,086).

The single-stranded nucleic acid is synthesized using a solid phase phosphoramidite synthesis method (see Nucleic Acids Res., 1993, vol. 30, pp. 2435-2443), deprotected and desalted on a NAP-5 column (Amersham Pharmacia Biotech, Piscataway, N.J.). The oligomer is purified using ion-exchange high performance liquid chromatography (IE-HPLC) on an Amersham Source 15Q column (1.0 cm, h·25 cm; Amersham Pharmacia Biotech, Piscataway, N.J.) using a 15 min step-linear gradient. The gradient varies from 90:10 Buffers A:B to 52:48 Buffers A:B, where Buffer A is 100 mM Tris pH 8.5 and Buffer B is 100 mM Tris pH 8.5, 1 M NaCl. Samples are monitored at 260 nm and peaks corresponding to the full-length the oligonucleotide species are collected, pooled, desalted on a NAP-5 column, and lyophilized.

The purity of each single-stranded nucleic acid is determined by capillary electrophoresis (CE) on Beckman PACE 5000 (Beckman Coulter, Inc., Fullerton, Calif.). The CE capillary has a 100 um inner diameter and contains ssDNA IOOR Gel (Beckman-Coulter). Typically, about 0.6 nmol of the oligonucleotide is injected into a capillary, run in an electric field of 444 V/cm and detected by UV absorbance at 260 nm. A denatured Tris-Borate-7 M-urea running buffer is purchased from Beckman-Coulter. The single-stranded nucleic acid that is at least 90% pure as assessed by CE for use in experiments described below is obtained. Compound identity is verified by matrix-assisted laser desorption ionization time-of-flight (MALDI-TOF) mass spectroscopy on a Voyager DE™ Biospectometry Work Station (Applied Biosystems, Foster City, Calif.) following the manufacturer's recommended protocol. Relative molecular mass of the single-stranded nucleic acid can be obtained, within 0.2% of expected molecular mass.

The single-stranded nucleic acid is resuspended at a 100 µM concentration in a buffer consisting of 100 mM potassium acetate, 30 mM HEPES, pH 7.5. Complementary sense and antisense strands are mixed in equal molar amounts to yield a final solution of 50 µM of the double-stranded nucleic acid. Samples are heated to 95° C. for 5 minutes and allowed to cool to room temperature before use. The double-stranded nucleic acid is stored at −20° C. The single-stranded nucleic acid is stored lyophilized or in nuclease-free water at −80° C.

Specific examples of the double-stranded nucleic acid which is used in the present invention are shown in Table 3. Incidentally, sugars attached to bases appended with r, m and d are ribose, ribose wherein a hydroxyl group at position 2' is replaced by —O-methyl and deoxyribose, respectively.

TABLE 3

| Target Sequence of KRAS mRNA (5' to 3') | SEQ ID No. | Sequence of siRNA antisense (upper) and sense (under) (5' to 3') | SEQ ID No. | siRNA Name |
|---|---|---|---|---|
| GUGUAUUUGCCAUAAAUAAUA | 1 | mGmUrAmUrUmUrGmCrCrArUmArAmArUmA rAmUrArCrUrAmAdAdT | 4 | A |
|  |  | mAmUmUmUrArGrUrArUrUmArUmUrUrArUrG rGrCrArArUrAmCrAmC | 5 |  |
| UACUAAAUCAUUUGAAGAUAU | 2 | mCmUrAmArAmUrCmArUrUmGrAmArGmA rUmAmUrUrCrAmCdCdA | 6 | B |
|  |  | rUmGrGrUrGrArArUrArUmCrUmUrCmArAmA rUmGrAmUrUmUrAmGmUmA | 7 |  |

TABLE 3-continued

| Target Sequence of KRAS mRNA (5' to 3') | SEQ ID No. | Sequence of siRNA antisense (upper) and sense (under) (5' to 3') | SEQ ID No. | siRNA Name |
|---|---|---|---|---|
| AUACUAAAUCAUUUGAAGAUA | 3 | mAmCmUrArArArUrCrArUrUrUrGrArAmGmA mUrArUrUrCrAdCdC mGmGmUmGrArArUrArUrCmUrUmCrArArArU rGrArUrUrUmArGmUrAmU | 8 9 | C |
| GUGUAUUUGCCAUAAAUAAUA | 1 | mGmUrAmUrUmUrGmCrCrArUmArAmArUmA rAmUrArCrUrAmAdAdT mAmUmUmUrArGrUrArUrUmArUmUrUrArUrG rGrCrAmArAmUrAmCmAmC | 4 10 | D |
| GUGUAUUUGCCAUAAAUAAUA | 1 | mGmUrAmUrUmUrGmCrCrArUmArAmArUmA rAmUrArCrUrAmAdAdT mAmUmUmUrArGrUrArUrUmArUmUrUmArU mGrGmCrAmArAmUrAmCmAmC | 4 11 | E |

The lipid particle in the present invention comprises Compound (I) or Compounds (I) and (II); and a double-stranded nucleic acid. Examples of the lipid particle include a complex of Compound (I) or Compounds (I) and (II) and a double-stranded nucleic acid; a lipid particle containing a complex between a combination having Compound (I) or Compounds (I) and (II) with neutral lipid and/or a polymer and a double-stranded nucleic acid; and a lipid particle constituted of the complex and a lipid membrane for encapsulating the complex therein. The lipid membrane may be either a lipid monolayer membrane (lipid monomolecular membrane) or a lipid bilayer membrane (lipid bimolecular membrane). Incidentally, the lipid membrane may contain Compounds (I), Compounds (II), a neutral lipid, and/or a polymer. In addition, the lipid particle may contain a cationic lipid other than Compounds (I) and (II) in the complex, and/or the lipid membrane.

In addition, further examples of the lipid particle include those constituted of a complex between Compound (II) and a double-stranded nucleic acid, or a complex between a combination having Compound (II) with a neutral lipid and/or a polymer and a double-stranded nucleic acid, and a lipid bilayer membrane for encapsulating the complex, and containing Compounds (I) in the lipid membrane. Also this case, the lipid membrane may be either a lipid monolayer membrane (lipid monomolecular membrane) or a lipid bilayer membrane (lipid bimolecular membrane). Incidentally, the lipid membrane may contain Compounds (II), a neutral lipid, and/or a polymer. In addition, the lipid particle may contain a cationic lipid other than Compounds (I) and (II) in the complex, and/or the lipid membrane.

Examples of a form of the complex in all of the present invention, include a complex between a double-stranded nucleic acid and a membrane composed of a lipid monolayer (reversed micelle), a complex between a double-stranded nucleic acid and liposome, and a complex between a double-stranded nucleic acid and a micelle. Of these, a complex between a double-stranded nucleic acid and a membrane composed of a lipid monolayer and a complex between a double-stranded nucleic acid and a liposome are preferable.

Examples of the lipid particle constituted of the complex and a lipid bilayer membrane for encapsulating the complex therein include a liposome constituted of the complex and a lipid bilayer membrane for encapsulating the complex.

Incidentally, in the lipid particle in the present invention, each of Compounds (I) and (II) may be used solely in kind or in admixture of plural kinds thereof. In addition, in Compound (I) and/or Compound (II), a cationic lipid other than Compounds (I) and (II) may be mixed.

Examples of the cationic lipid other than Compounds (I) and (II) include DOTMA, DOTAP, and the like as disclosed in JP-A-61-161246 (corresponding to U.S. Pat. No. 5,049,386); N-[1-(2,3-dioleyloxypropyl)]-N,N-dimethyl-N-hydroxyethylammonium bromide (DORIE), 2,3-dioleyloxy-N-[2-(spermine carboxamido)ethyl]-N,N-dimethyl-1-propanaminium trifluoroacetate (DOSPA), and the like as disclosed in International Publication Nos. WO91/16024 and WO97/019675; DLinDMA and the like as disclosed in International Publication No. WO2005/121348; and DLin-K-DMA and the like as disclosed in International Publication No. WO2009/086558. The cationic lipid other than Compounds (I) and (II) is preferably a cationic lipid having a tertiary amine site having two unsubstituted alkyl groups, or a quaternary ammonium site having three unsubstituted alkyl groups, such as DOTMA, DOTAP, DORIE, DOSPA, DLinDMA, and DLin-K-DMA; and more preferably a cationic lipid having the tertiary amine site. The unsubstituted alkyl group in each of the tertiary amine site and the quaternary ammonium site is more preferably a methyl group.

The lipid particle in the present invention can be produced by a known production method or a method similar thereto and may be a lipid particle produced by any production method. For example, in the production of a liposome as one of lipid particles, a known preparation method of a liposome can be applied. Examples of the known preparation method of a liposome include a liposome preparation method by Bangham et al. (see J. Mol. Biol., 1965, Vol. 13, pp. 238-252); an ethanol injection method (see J. Cell Biol., 1975, Vol. 66, pp. 621-634); a French press method (see FEBS Lett., 1979, Vol. 99, pp. 210-214); a freeze-thawing method (see Arch. Biochem. Biophys., 1981, Vol. 212, pp. 186-194); a reverse phase evaporation method (see Proc. Natl. Acad. Sci. USA, 1978, Vol. 75, pp. 4194-4198); and a pH gradient method (see, for example, Japanese Patent Nos. 2572554 and 2659136, etc.) As a solution which disperses the liposome in the production of liposome, for example, water, an acid, an alkali, a variety of buffer solution, a saline, an amino acid infusion, and the like can be used. In addition, in the production of a liposome, it is also possible to add an antioxidant, for example, citric acid, ascorbic acid, cysteine, ethylenediaminetetraacetic acid (EDTA), etc., an isotonic agent, for example, glycerin, glucose, sodium chloride, etc., or the like. In addition, the liposome can also be produced by dissolving a lipid or the like in an organic solvent, for example, ethanol etc., distilling off the solvent, adding a saline or the like thereto, and stirring and shaking the mixture, thereby forming a liposome.

In addition, the lipid particle in the present invention can be produced by, for example, a method in which Compound (I), Compounds (I) and (II), Compound (I) and a cationic lipid other than Compounds (I) and (II), or Compounds (I) and (II) and a cationic lipid other than Compounds (I) and (II) are dissolved in chloroform in advance; subsequently, an aqueous solution of a double-stranded nucleic acid and methanol are added thereto followed by mixing to form a cationic lipid/double-stranded nucleic acid complex; furthermore, the chloroform layer is taken out, to which are then added a polyethylene glycolated phospholipid, a neutral lipid, and water to form a water-in-oil type (W/O) emulsion; and the emulsion is treated by a reverse phase evaporation method (see JP-T-2002-508765); a method in which a double-stranded nucleic acid is dissolved in an acidic electrolyte aqueous solution, to which is then added a lipid (in ethanol); an ethanol concentration is decreased to 20 v/v %, thereby preparing a liposome including the double-stranded nucleic acid therein; the liposome is subjected to sizing filtration and dialysis to remove the excessive ethanol; and the resulting sample is further subjected to dialysis while increasing the pH, thereby removing the double-stranded nucleic acid attached onto the liposome surface (see JP-T-2002-501511 and *Biochimica et Biophysica Acta*, 2001, Vol. 1510, pp. 152-166); and the like.

Among the lipid particles in the present invention, the liposome constituted of a complex and a lipid bilayer membrane having the complex encapsulated therein can be produced according to a production method described in, for example, International Publication Nos. WO02/28367 and WO2006/080118, etc.

In addition, among the lipid particles in the present invention, for example, the lipid particle constituted of a complex between Compound (I) or Compounds (I) and (II) and the double-stranded nucleic acid, or a complex between a combination having Compound (I) or Compounds (I) and (II) with a neutral lipid and/or a polymer and a double-stranded nucleic acid, and a lipid membrane for encapsulating the complex, the lipid membrane containing Compound (I), Compound (II), and/or a cationic lipid other than Compounds (I) and (II); the lipid particle constituted of a complex between Compound (II) and a double-stranded nucleic acid, or a complex between a combination having Compound (II) with a neutral lipid and/or a polymer and a double-stranded nucleic acid, and a lipid bilayer membrane for encapsulating the complex, the lipid membrane containing Compounds (I) or Compounds (I) and (II); and the like can be obtained by producing the respective complexes in accordance with a production method described in International Publication Nos. WO02/28367 and WO2006/080118, etc., dispersing the complexes in water or an 0 to 20% ethanol aqueous solution without dissolving them (solution A), separately dissolving the respective lipid components in an ethanol aqueous solution (solution B), mixing the solution A and the solution B, and further properly adding water thereto. In addition, each of Compound (I), Compound (II), and the cationic lipid other than Compounds (I) and (II) in the solution A and B may be used solely in kind or in admixture of plural kinds thereof.

Incidentally, in the present invention, those in which during the production and after the production of the lipid particle constituted of a complex between Compound (I) or Compounds (I) and (II) and a double-stranded nucleic acid, or a complex between a combination having Compound (I) or Compounds (I) and (II) with a neutral lipid and/or a polymer and a double-stranded nucleic acid, and a lipid membrane for encapsulating the complexe therein, the lipid membrane containing Compound (I), Compound (II), or a cationic lipid other than Compounds (I) and (II); the lipid particle constituted of a complex between Compound (II) and a nucleic acid, or a complex between a combination having Compound (II) with a neutral lipid and/or a polymer and a nucleic acid, and a lipid membrane for encapsulating the complex therein, and the lipid membrane containing Compound (I) or Compounds (I) and (II); and the like, an electrostatic interaction between the double-stranded nucleic acid in the complex and the cationic lipid in the lipid membrane, or fusion between the cationic lipid in the complex and the cationic lipid in the lipid membrane has caused displacement of the structures of the complex and the membrane are also included in the lipid particle constituted of a complex between Compound (I) or Compounds (I) and (II) and a double-stranded nucleic acid, or a complex between a combination having Compound (I) or Compounds (I) and (II) with a neutral lipid and/or a polymer and a double-stranded nucleic acid, and a lipid membrane for encapsulating the complex therein, the lipid membrane containing Compound (I), Compound (II), or a cationic lipid other than Compounds (I) and (II); the lipid particle constituted of a complex between Compound (II) and a nucleic acid, or a complex between a combination having Compound (II) with a neutral lipid and/or a polymer and a nucleic acid, and a lipid membrane for encapsulating the complex therein, and the lipid membrane containing Compound (I) or Compounds (I) and (II); and the like.

The lipid particle in the present invention is more preferably a lipid particle constituted of a complex between Compound (I) or Compounds (I) and (II) and a double-stranded nucleic acid, a complex between a combination having Compound (I) or Compounds (I) and (II) with a neutral lipid and/or a polymer and a double-stranded nucleic acid, and a lipid membrane for encapsulating the complex therein, the lipid membrane containing Compound (I), Compound (II), or a cationic lipid other than Compounds (I) and (II); still more preferably a lipid particle constituted of a complex between Compound (I) or Compounds (I) and (II) and a double-stranded nucleic acid, a complex between a combination having Compound (I) or Compounds (I) and (II) with a neutral lipid and/or a polymer and a double-stranded nucleic acid, and a lipid membrane for encapsulating the complex therein, the lipid membrane containing Compound (I) or Compounds (I) and (II); and yet still more preferably a lipid particle constituted of a complex between Compound (I) or a combination having Compound (I) with a neutral lipid and a double-stranded nucleic acid and a lipid membrane for encapsulating the complex therein, the lipid membrane containing Compound (I), or a lipid particle constituted of a complex between a combination having Compounds (I) and (II) with a neutral lipid and a double-stranded nucleic acid and a lipid membrane for encapsulating the complex therein, the lipid membrane containing Compounds (I) and (II).

A total number of molecules of Compounds (I) and (II) in the complex is preferably 0.5 to 4 parts, more preferably 1.5 to 3.5 parts, further more preferably 2 to 3 parts relative to 1 part by a number of phosphorus atoms in the double-stranded nucleic acid. Further, a total number of molecules of Compounds (I) and (II), and the cationic lipid other than Compounds (I) and (II) in the complex is preferably 0.5 to 4 parts, more preferably 1.5 to 3.5 parts, further more preferably 2 to 3 parts relative to 1 part by a number of phosphorus atoms in the double-stranded nucleic acid.

In the case where the lipid particle of the present invention is constituted of the complex and the lipid membrane for encapsulating the complex therein, a total number of molecules of Compounds (I) and (II) in the lipid particle is preferably 1 to 10 parts, more preferably 2.5 to 9 parts, further more preferably 3.5 to 8 parts relative to 1 part by a number of phosphorus atoms in the double-stranded nucleic acid. Further, a total number of molecules of Compounds (I) and (II), and the cationic lipid other than Compounds (I) and (II) in the lipid particle is preferably 1 to 10 parts, more preferably 2.5 to 9 parts, further more preferably 3.5 to 8 parts relative to 1 part by a number of phosphorus atoms in the double-stranded nucleic acid.

The neutral lipid may be any lipid including a simple lipid, a complex lipid, and a derived lipid. Examples thereof include a phospholipid, a glyceroglycolipid, a sphingoglycolipid, a sphingoid, and a sterol. However, it should not be construed that the present invention is limited thereto.

In the case where the lipid particle of the present invention contains the neutral lipid, a total number of molecules of the neutral lipid is preferably 0.1 to 1.8 parts, more preferably 0.3 to 1.1 parts, further more preferably 0.4 to 0.9 parts relative to 1 part by a total number of molecules of Compounds (I) and (II), and the cationic lipid other than Compounds (I) and (II). The lipid particle either in the present invention may contain the neutral lipid in the complex, or in the lipid membrane for encapsulating the complex therein. It is more preferable that the neutral lipid is at least contained in the lipid membrane; and still more preferable that the neutral lipid is contained both in the complex and in the lipid membrane.

Examples of the phospholipid in the neutral lipid include natural or synthetic phospholipids such as phosphatidylcholines (specifically, soybean phosphatidylcholine, egg yolk phosphatidylcholine (EPC), distearoyl phosphatidylcholine (DSPC), dipalmitoyl phosphatidylcholine (DPPC), palmitoyloleoyl phosphatidylcholine (POPC), dimyristoyl phosphatidylcholine (DMPC), dioleoyl phosphatidylcholine (DOPC), etc.), phosphatidylethanolamines (specifically, distearoyl phosphatidylethanolamine (DSPE), dipalmitoyl phosphatidylethanolamine (DPPE), dioleoyl phosphatidylethanolamine (DOPE), dimyristoyl phosphoethanolamine (DMPE), 16-0-monomethyl PE, 16-0-dimethyl PE, 18-1-trans PE, palmitoyloleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyloleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphate, etc.), glycerophosphonolipids, sphingophosphonolipids, natural lecithins (specifically, egg yolk lecithin, soybean lecithin, etc.), and hydrogenated phospholipids (specifically, hydrogenated soybean phosphatidylcholine etc.)

Examples of the glyceroglycolipid in the neutral lipid include sulfoxyribosyl glyceride, diglycosyl diglyceride, digalactosyl diglyceride, galactosyl diglyceride, and glycosyl diglyceride.

Examples of the sphingoglycolipid in the neutral lipid include galactosyl cerebroside, lactosyl cerebroside, and ganglioside.

Examples of the sphingoid in the neutral lipid include sphingan, icosasphingan, sphingosine, and derivatives thereof. Examples of the derivative include those in which —NH$_2$ of sphingan, icosasphingan, sphingosine, or the like is replaced with —NHCO(CH$_2$)$_x$CH$_3$ (in the formula, x is an integer of from 0 to 18, with 6, 12, or 18 being preferable).

Examples of the sterol in the neutral lipid include cholesterol, dihydrocholesterol, lanosterol, β-sitosterol, campesterol, stigmasterol, brassicasterol, ergocasterol, fucosterol, and 3β-[N—(N',N'-dimethylaminoethyl)carbamoyl]cholesterol (DC-Choly.

The neutral lipid is preferably a phospholipid, a sterol or the like; more preferably phosphatidylcholine, phosphatidylethanolamine, or cholesterol; and still more preferably phosphatidylethanolamine, cholesterol, or a combination thereof.

The polymer may be one or more polymers selected from, for example, protein, albumin, dextran, polyfect, chitosan, dextran sulfate; and polymers, for example, such as poly-L-lysine, polyethyleneimine, polyaspartic acid, a copolymer of styrene and maleic acid, a copolymer of isopropylacrylamide and acrylpyrrolidone, polyethylene glycol modified dendrimer, polylactic acid, polylactic acid polyglycolic acid, and polyethylene glycolated polylactic acid, and salts thereof.

Here, the salt of the polymer includes, for example, a metal salt, an ammonium salt, an acid addition salt, an organic amine addition salt, an amino acid addition salt, and the like. Examples of the metal salt include alkali metal salts such as a lithium salt, a sodium salt and a potassium salt; alkaline earth metal salts such as a magnesium salt and a calcium salt; an aluminum salt; a zinc salt, and the like. Examples of the ammonium salt include salts of ammonium, tetramethylammonium, or the like. Examples of the acid addition salt include inorganates such as a hydrochloride, a sulfate, a nitrate, and a phosphate, and organates such as an acetate, a maleate, a fumarate, and a citrate. Examples of the organic amine addition salt include addition salts of morpholine, piperidine, or the like, and examples of the amino acid addition salt include addition salts of glycine, phenylalanine, aspartic acid, glutamic acid, lysine, or the like.

In addition, the lipid particle in the present invention preferably further contains a lipid conjugate or fatty acid conjugate of a water-soluble polymer. The lipid conjugate or fatty acid conjugate of a water-soluble polymer may be contained in the complex, or may be contained in the lipid membrane for encapsulating the complex therein. It is more preferable that the lipid conjugate or fatty acid conjugate of a water-soluble polymer is contained both in the complex and in the lipid membrane.

In the case where the lipid particle of the present invention contains the lipid conjugate or fatty acid conjugate of a water-soluble polymer, a total number of molecules of the lipid conjugate or fatty acid conjugate of a water-soluble polymer is preferably 0.05 to 0.3 parts, more preferably 0.07 to 0.25 parts, further more preferably 0.1 to 0.2 parts relative to 1 part by a total number of molecules of Compounds (I) and (II), and the cationic lipid other than Compounds (I) and (II).

The lipid conjugate or fatty acid conjugate of a water-soluble polymer is preferably a substance having such a dual character that a part of the molecule has properties of binding to other constituent component(s) of the lipid particle due to, for example, hydrophobic affinity, electrostatic interaction, or the like, and the other part has properties of binding to a solvent at the time of production of the lipid particle due to, for example, hydrophilic affinity, electrostatic interaction, or the like.

Examples of the lipid conjugate or fatty acid conjugate of a water-soluble polymer include products formed by means of binding of the neutral lipid as exemplified above in the definition of the lipid particle or Compounds (I) or (II), or a fatty acid, for example, stearic acid, palmitic acid, myristic acid, lauric acid, etc. with, for example, polyethylene glycol, polyglycerin, polyethyleneimine, polyvinyl alcohol, polyacrylic acid, polyacrylamide, oligosaccharide, dextrin, water-soluble cellulose, dextran, chondroitin sulfate, chitosan, polyvinylpyrrolidone, polyaspartic acid amide, poly-L-lysine, mannan, pullulan, oligoglycerol, or a derivative thereof, and salts thereof. More preferred examples thereof include lipid conjugates or fatty acid conjugates such as polyethylene glycol derivatives and polyglycerin derivatives, and salts thereof. Still more preferred examples thereof include lipid conjugates or fatty acid conjugates of a polyethylene glycol derivative, and salts thereof.

Examples of the lipid conjugate or fatty acid conjugate of a polyethylene glycol derivative include polyethylene glycolated lipids (specifically, polyethylene glycol-phosphatidylethanolamines (more specifically, 1,2-distearoyl-sn-glycero-3-phosphoethanolamine-N-[methoxy(polyethylene glycol)-2000] (PEG-DSPE), 1,2-dimyristoyl-sn-glycero-3-phosphoethanolamine-N—[methoxy(polyethylene glycol)-2000] (PEG-DMPE), etc.), polyoxyethylene hydrogenated castor oil 60, CREMOPHOR EL, and the like), polyethylene glycol sorbitan fatty acid esters (specifically, polyoxyethylene sorbitan monooleate, etc.), and polyethylene glycol fatty acid esters; preferred examples thereof include polyethylene glycolated lipids; and more preferred examples thereof include PEG-DSPE and PEG-DMPE.

Examples of the lipid conjugate or fatty acid conjugate of a polyglycerol derivative include polyglycerolated lipids (specifically, polyglycerol phosphatidyl ethanolamine and the like), polyglycerol fatty acid esters and the like, and more preferred examples thereof include polyglycerolated lipids.

In addition, in the lipid particle in the present invention, surface modification of the lipid particle with, for example, a water-soluble polymer, a polyoxyethylene derivative, etc. can be arbitrarily carried out [see ed. D. D. Lasic, F. Martin, *Stealth Liposomes*, CRC Press Inc., US, 1995, p. 93-102]. Examples of the polymer which can be used for the surface modification include dextran, pullulan, mannan, amylopectin, and hydroxyethyl starch. Examples of the polyoxyethylene derivative include polysorbate 80, Pluronic F68, polyoxyethylene hydrogenated castor oil 60, polyoxyethylene lauryl alcohol, and PEG-DSPE. The lipid conjugate or fatty acid conjugate of a water-soluble polymer can be contained in the complex and the lipid membrane in the lipid particle by means of the surface modification of the lipid particle.

An average particle diameter of the lipid particle in present invention can be freely selected upon demand. It is preferable to adjust the average particle diameter to a diameter shown below. Examples of a method of adjusting the average particle diameter include an extrusion method, a method in which a large multilamellar liposome vesicle (MLV) and the like is mechanically pulverized (specifically using Manton-gaulin, a microfluidizer or the like) (see "Emulsion and Nanosuspensions for the Formulation of Poorly Soluble Drugs", edited by R. H. Muller, S. Benita and B. Bohm, Scientific Publishers, Stuttgart, Germany, pp. 267-294, 1998) and the like.

As for the size of the lipid particle in the present invention, an average particle diameter is preferably from about 10 nm to 1,000 nm, more preferably from about 30 nm to 300 nm, and still more preferably from about 50 nm to 200 nm.

By administering the composition of the present invention to a mammalian cell, the double-stranded nucleic acid in the composition of the present invention can be introduced into the cell.

A method for introducing the composition of the present invention to a mammalian cell in vivo may be carried out according to the known procedures of known transfection capable of being carried out in vivo. For example, by intravenous administration of the composition of the present invention to a mammal including human, the composition can be delivered to, for example, an organ or a site involving cancer or inflammation, and the double-stranded nucleic acid in the composition of the present invention can be introduced into cells of the organ or the site. The organ or the site involving cancer or inflammation is not particularly limited. Examples thereof include stomach, large intestine, liver, lungs, spleen, pancreas, kidneys, bladder, skin, blood vessel, and eye ball. Of these, large intestine and pancreas are preferable. In addition, by intravenous administration of the composition of the present invention to a mammal including human, the composition can be delivered to, for example, blood vessel, liver, lungs, spleen, and/or kidneys, and the double-stranded nucleic acid in the composition of the present invention can be introduced into the cells of the organ or the site. The blood vessel, liver, lung, spleen, and/or kidney cells may be a normal cell, too.

When the double-stranded nucleic acid in the composition of the present invention is introduced into the cells of the organ or the site, it is possible to reduce the expression of a RAS gene in the cells, thereby treating a KRAS-associated disease, for example, leukemia, melanoma, blastoma, cancer, tumor, adenoma, or the like.

That is, by administering the composition of the present invention to a mammal, it is possible to reduce the expression of a RAS gene, thereby treating a RAS-associated disease, for example, leukemia, melanoma, blastoma, cancer, tumor, adenoma, or the like. The administration target is preferably human.

In addition, the composition of the present invention can also be used as a tool to validate the effectiveness on KRAS silencing in vivo models, as to an agent for the treatment or prevention of cancer.

In the case where the composition of the present invention is used as a therapeutic agent or a preventive agent for cancer, it is desirable that an administration route that is the most effective for the treatment is used. As the administration route, intravenous administration and intramuscular administration are preferable, and intravenous administration is more preferable.

The dose may vary depending upon conditions and age of the subject, the administration route, and the like. For example, the administration may be made such that the dose is, for example, from about 0.1 µg to 1,000 mg per day in terms of the double-stranded nucleic acid.

As a preparation suitable for the intravenous administration or intramuscular administration, for example, an injection can be exemplified, and it is also possible to use a dispersion liquid of the lipid particle prepared by the foregoing method as it is in the form of, for example, an injection or the like. However, the dispersion liquid can also be used after removing the solvent from it by, for example, filtration, centrifugation, or the like, or after lyophilizing it or the dispersion liquid supplemented with an excipient such as mannitol, lactose, trehalose, maltose, or glycine.

In the case of an injection, it is preferable that an injection is prepared by mixing, for example, water, an acid, an alkali, a variety of buffer solution, a saline, an amino acid infusion, or the like with the foregoing dispersion liquid of the lipid particle or the foregoing composition obtained by removing the solvent or lyophilization. In addition, it is also possible to prepare an injection by adding an antioxidant such as citric acid, ascorbic acid, cysteine, or EDTA, an isotonic agent such as glycerin, glucose, or sodium chloride, or the like thereto. In addition, it can also be cryopreserved by adding a cryopreservation agent such as glycerin thereto.

Next, the present invention is specifically described with reference to the following Examples, Referential Examples and Test Examples. However, it should not be construed that the present invention is limited to these Examples and Test Examples.

Incidentally, proton nuclear magnetic resonance spectra ($^1$H NMR) shown in Referential Examples are those measured at 270 MHz, 300 MHz, or 400 MHz, and there may be the case where an exchangeable proton is not distinctly observed depending upon the compound and measuring conditions. Incidentally, regarding the expression for multiplicity of a signal is a usually used expression is used. The term "br" indicates an apparently broad signal.

Referential Example 1

Methyl di((9Z,12Z)-octadeca-9,12-dienyl)amine (Compound II-1)

To methylamine (manufactured by Aldrich, about 2 mol/L tetrahydrofuran solution, 10.5 mL, 21.0 mmol), (9Z,12Z)-octadeca-9,12-dienyl methanesulfonate (manufactured by Nu-Chek Prep, Inc., 1.03 g, 3.00 mmol) was added, and the contents were heated with stirring at 150° C. for 90 minutes by using a microwave reaction apparatus. The reaction solution was diluted with ethyl acetate, washed successively with a 2 mol/L sodium hydroxide aqueous solution and saturated salt water, and dried over anhydrous magnesium sulfate. Thereafter, the resultant was filtered and concentrated under reduced pressure to obtain a crude product of methyl ((9Z,12Z)-octadeca-9,12-dienyl)amine.

To the obtained crude product, (9Z,12Z)-octadeca-9,12-dienyl methanesulfonate (manufactured by Nu-Chek Prep, Inc., 0.93 g, 2.70 mmol) and a 50% sodium hydroxide aqueous solution (0.960 g, 12.0 mmol) were added, and the contents were heated with stirring at 135° C. for 60 minutes on an oil bath. After cooling to room temperature, the reaction solution was diluted with ethyl acetate, washed successively with water and saturated salt water, and dried over anhydrous magnesium sulfate. Thereafter, the resultant was filtered and concentrated under reduced pressure. The obtained residue was purified by means of silica gel column chromatography (chloroform/methanol:100/0 to 97/3), thereby obtaining Compound II-1 (1.07 g, 67.2%).

ESI-MS m/z: 529 (M+H)$^+$; $^1$H-NMR (CDCl$_3$) δ: 0.89 (t, J=6.7 Hz, 6H), 1.29 (br s, 32H), 1.40 to 1.51 (m, 4H), 1.97 to 2.06 (m, 8H), 2.20 (s, 3H), 2.30 (t, J=7.6 Hz, 4H), 2.77 (t, J=5.8 Hz, 4H), 5.28 to 5.43 (m, 8H)

Referential Example 2

Methyl di((Z)-hexadec-9-enyl)amine (Compound II-2)

Compound II-2 (0.491 g, 51.6%) was obtained in the same manner as that in Referential Example 1, by using methylamine (manufactured by Aldrich, about 2 mol/L tetrahydrofuran solution, 10.0 mL, 20.0 mmol) and (Z)-hexadec-9-enyl methanesulfonate (manufactured by Nu-Chek Prep, Inc., 1.21 g, 3.80 mmol).

ESI-MS m/z: 477 (M+H)$^+$; $^1$H-NMR (CDCl$_3$) δ: 0.88 (t, J=6.7 Hz, 6H), 1.29 (br s, 36H), 1.46 to 1.57 (m, 4H), 1.97 to 2.05 (m, 8H), 2.33 (s, 3H), 2.45 (t, J=7.9 Hz, 4H), 5.29 to 5.41 (m, 4H)

Referential Example 3

Methyl di((11Z,14Z)-icosa-11,14-dienyl)amine (Compound II-3)

Compound II-3 (1.27 g, 54.4%) was obtained in the same manner as that in Referential Example 1, by using methylamine (manufactured by Aldrich, about 2 mol/L tetrahydrofuran solution, 16.0 mL, 32.0 mmol) and (11Z,14Z)-icosa-11,14-dienyl methanesulfonate (manufactured by Nu-Chek Prep, Inc., 2.98 g, 8.00 mmol).

ESI-MS m/z: 585 (M+H)$^+$; $^1$H-NMR (CDCl$_3$) δ: 0.89 (t, J=6.7 Hz, 6H), 1.27 (br s, 40H), 1.39 to 1.51 (m, 4H), 2.01 to 2.09 (m, 8H), 2.20 (s, 3H), 2.30 (t, J=7.6 Hz, 4H), 2.79 (d, J=6.3 Hz, 4H), 5.28 to 5.43 (m, 8H)

Referential Example 4

Di((9Z,12Z)-octadeca-9,12-dienyl)amine (Compound II-4)

Compound II-4 (0.838 g, 36.2%) was obtained in the same manner as that in Referential Example 1, by using ammonia (manufactured by Tokyo Chemical Industry Co., Ltd., about 2 mol/L methanol solution, 18.0 mL, 36.0 mmol) and (9Z,12Z)-octadeca-9,12-dienyl methanesulfonate (manufactured by Nu-Chek Prep, Inc., 2.79 g, 8.10 mmol).

ESI-MS m/z: 515 (M+H)$^+$; $^1$H-NMR (CDCl$_3$) δ: 0.89 (t, J=6.9 Hz, 6H), 1.30 (br s, 33H), 1.41 to 1.54 (m, 4H), 2.01 to 2.09 (m, 8H), 2.59 (t, J=7.2 Hz, 4H), 2.77 (d, J=5.6 Hz, 4H), 5.28 to 5.43 (m, 8H)

Referential Example 5

Di((Z)-octadec-9-enyl)amine (Compound II-5)

Compound II-5 (0.562 g, 36.2%) was obtained in the same manner as that in Referential Example 1, by using ammonia (manufactured by Tokyo Chemical Industry Co., Ltd., about 2 mol/L methanol solution, 12.0 mL, 24.0 mmol) and (Z)-octadec-9-enyl methanesulfonate (manufactured by Nu-Chek Prep, Inc., 1.87 g, 5.40 mmol).

ESI-MS m/z: 519 (M+H)$^+$; $^1$H-NMR (CDCl$_3$) δ: 0.88 (t, J=6.7 Hz, 6H), 1.29 (br s, 45H), 1.41 to 1.52 (m, 4H), 1.97 to 2.05 (m, 8H), 2.58 (t, J=7.2 Hz, 4H), 5.28 to 5.40 (m, 4H)

Referential Example 6

Methyl di((Z)-octadec-9-enyl)amine (Compound II-6)

Compound II-6 (1.20 g, 70.2%) was obtained in the same manner as that in Referential Example 1, by using methylamine (manufactured by Aldrich, about 2 mol/L tetrahydrofuran solution, 11.2 mL, 22.4 mmol) and (Z)-octadec-9-enyl methanesulfonate (manufactured by Nu-Chek Prep, Inc., 2.11 g, 6.09 mmol).

ESI-MS m/z: 533 (M+H)$^+$; $^1$H-NMR (CDCl$_3$) δ: 0.88 (t, J=6.6 Hz, 6H), 1.27 (br s, 44H), 1.39 to 1.50 (m, 4H), 1.97 to 2.06 (m, 8H), 2.20 (s, 3H), 2.30 (t, J=7.6 Hz, 4H), 5.28 to 5.40 (m, 4H)

Referential Example 7

Trans-1-(tert-butoxycarbonyl)-3,4-bis((Z)-octadec-9-enoyloxy)methyl)pyrrolidine (Compound VII-1)

Tert-butyl trans-3,4-bis(hydroxymethyl)pyrrolidine-1-carboxylate (156 mg, 0.674 mmol) as synthesized by reference to International Publication No. WO2006/100036 was dissolved in dichloromethane (6 mL), to which were then added oleic acid (manufactured by Tokyo Chemical Industry Co., Ltd., 419 mg, 1.48 mmol), water soluble carbodiimide (WSCD, manufactured by Kokusan Chemical Co., Ltd., 297 mg, 1.55 mmol), and 4-dimethylaminopyridine (manufactured by Tokyo Chemical Industry Co., Ltd., DMAP 20.6 mg, 0.169 mmol), and the contents were stirred at room temperature day and night. To the reaction solution, saturated sodium hydrogencarbonate aqueous solution was added, followed by extraction with ethyl acetate. The organic layer was washed with water and saturated salt water and dried over anhydrous magnesium sulfate, followed by concentration under reduced pressure. The residue was purified by means of silica gel column chromatography (hexane/chloroform:50/50 to 0/100), thereby obtaining Compound VII-1 (280 mg, 54.6%).

ESI-MS m/z: 761 (M+H)$^+$; $^1$H-NMR (CDCl$_3$) δ: 0.88 (t, J=6.6 Hz, 6H), 1.25 to 1.46 (m, 36H), 1.46 (s, 9H), 1.46 to 1.66 (m, 8H), 1.97 to 2.04 (m, 8H), 2.27 to 2.38 (m, 6H), 3.10 to 3.23 (m, 2H), 3.53 to 3.66 (m, 2H), 4.03 (dd, J=10.8, 6.0 Hz, 2H), 4.14 (dd, J=10.8, 6.0 Hz, 2H), 5.28 to 5.40 (m, 4H)

Referential Example 8

Trans-1-(tert-butoxycarbonyl)-3,4-bis(((9Z,12Z)-octadeca-9,12-dienoyloxy)methyl)pyrrolidine (Compound VII-2)

Compound VII-2 (351 mg, 71.7%) was obtained in the same manner as that in Referential Example 7, by using tert-butyl trans-3,4-bis(hydroxymethyl)pyrrolidine-1-carboxylate (150 mg, 0.674 mmol) as synthesized by reference to International Publication No. WO2006/100036 and linoleic acid (manufactured by Aldrich, 400 mg, 1.48 mmol).

ESI-MS m/z: 757 (M+H)$^+$; $^1$H-NMR (CDCl$_3$) δ: 0.89 (t, J=6.8 Hz, 6H), 1.21 to 1.45 (m, 26H), 1.46 (s, 9H), 1.47 to 1.68 (m, 6H), 2.05 (q, J=6.7 Hz, 8H), 2.26 to 2.38 (m, 6H), 2.77 (t, J=5.9 Hz, 4H), 3.10 to 3.23 (m, 2H), 3.53 to 3.66 (m, 2H), 4.03 (dd, J=11.0, 6.0 Hz, 2H), 4.14 (dd, J=11.0, 6.0 Hz, 2H), 5.28 to 5.43 (m, 8H)

Referential Example 9

Trans-3,4-bis(((Z)-octadec-9-enoyloxy)methyl)pyrrolidine (Compound I-1)

Compound VII-1 (278 mg, 0.366 mmol) obtained in Referential Example 7 was dissolved in dichloromethane (6 mL), to which was then added trifluoroacetic acid (0.563 mL, 7.31 mmol), and the contents were stirred at room temperature for 3 hours. To the reaction mixture, a saturated sodium hydrogencarbonate aqueous solution was added, and the aqueous layer was extracted with chloroform. The organic layer was washed with saturated salt water and dried over anhydrous magnesium sulfate. Thereafter, the resultant was filtered and concentrated under reduced pressure. The obtained residue was dissolved in a small amount of methanol, and the solution was adsorbed onto an upper part of BONDESIL-SCX (manufactured by Varian Medical Systems Inc., 6 g) filled in a plastic column, followed by washing with methanol. Subsequently, the target material was eluted with an ammonia/methanol solution (manufactured by Tokyo Chemical Industry Co., Ltd., 2 mol/L). A fraction containing the target material was concentrated under reduced pressure, thereby obtaining Compound I-1 (162 mg, 67.2%).

ESI-MS m/z: 661 (M+H)$^+$; $^1$H-NMR (CDCl$_3$) δ: 0.88 (t, J=6.6 Hz, 6H), 1.27 to 1.35 (m, 40H), 1.56 to 1.64 (m, 4H), 2.01 (q, J=5.9 Hz, 8H), 2.09 to 2.16 (m, 2H), 2.30 (t, J=7.5 Hz, 4H), 2.72 (dd, J=11.3, 5.5 Hz, 2H), 3.11 (dd, J=11.3, 7.1 Hz, 2H), 3.99 to 4.12 (m, 4H), 5.29 to 5.40 (m, 4H)

Referential Example 10

Trans-3,4-bis(((9Z,12E)-octadeca-9,12-dienoyloxy)methyl)pyrrolidine (Compound I-2)

Compound I-2 (224 mg, 73.6%) was obtained in the same manner as that in Referential Example 9, by using Compound VII-2 (350 mg, 0.463 mmol) obtained in Referential Example 8.

ESI-MS m/z: 657 (M+H)$^+$; $^1$H-NMR (CDCl$_3$) δ: 0.89 (t, J=6.8 Hz, 6H), 1.26 to 1.40 (m, 28H), 1.57 to 1.66 (m, 4H), 2.05 (q, J=6.6 Hz, 8H), 2.09 to 2.17 (m, 2H), 2.31 (t, J=7.5 Hz, 4H), 2.72 (dd, J=11.3, 6.0 Hz, 2H), 2.77 (t, J=6.2 Hz, 4H), 3.11 (dd, J=11.3, 7.3 Hz, 2H), 3.99 to 4.13 (m, 4H), 5.28 to 5.43 (m, 8H)

Referential Example 11

Trans-1-methyl-3,4-bis(((9Z,12Z)-octadeca-9,12-dienoyloxy)methyl)pyrrolidine (Compound I-3)

Compound I-2 (80 mg, 0.12 mmol) obtained in Referential Example 10 was dissolved in 1,2-dichloroethane (1.5 mL) and methanol (1.5 mL), to which were then added formaldehyde (0.091 mL, 1.22 mmol) and sodium triacetoxyborohydride (manufactured by Acros Organics, 129 mg, 0.610 mmol) in portions, and the contents were stirred at room temperature for 1.5 hours. To the reaction solution, a saturated sodium hydrogencarbonate aqueous solution was added, and the aqueous layer was extracted with ethyl acetate. The organic layer was washed with a saturated salt water and dried over anhydrous magnesium sulfate. Thereafter, the resultant was filtered and concentrated under reduced pressure. The obtained residue was purified by means of silica gel column chromatography (chloroform/methanol:100/0 to 93/7), thereby obtaining Compound I-3 (66 mg, 81%).

ESI-MS m/z: 671 (M+H)$^+$; $^1$H-NMR (CDCl$_3$) δ: 0.89 (t, J=6.8 Hz, 6H), 1.25 to 1.40 (m, 28H), 1.57 to 1.66 (m, 4H), 2.05 (q, J=6.6 Hz, 8H), 2.13 to 2.24 (m, 2H), 2.27 to 2.37 (m, 9H), 2.66 (dd, J=9.2, 7.3 Hz, 2H), 2.77 (t, J=5.7 Hz, 4H), 3.99 to 4.12 (m, 4H), 5.28 to 5.43 (m, 8H)

Referential Example 12

Trans-1-methyl-3,4-bis(((Z)-octadec-9-enoyloxy)methyl)pyrrolidine (Compound I-4)

Compound I-4 (47 mg, 92%) was obtained in the same manner as that in Referential Example 11, by using Compound I-1 (50 mg, 0.076 mmol) obtained in Referential Example 9.

ESI-MS m/z: 675 (M+H)$^+$; $^1$H-NMR (CDCl$_3$) δ: 0.88 (t, J=6.6 Hz, 6H), 1.26 to 1.35 (m, 40H), 1.56 to 1.65 (m, 4H), 2.01 (q, J=5.5 Hz, 8H), 2.15 to 2.24 (m, 2H), 2.27 to 2.37 (m, 9H), 2.67 (dd, J=9.3, 7.1 Hz, 2H), 3.99 to 4.12 (m, 4H), 5.29 to 5.40 (m, 4H)

Example 1

A preparation was produced in the following manner by using Compound II-1 obtained in Referential Example 1 and Compound I-3 obtained in Referential Example 11 and also using siRNA Nos. A to C in Table 3.

Each of the double-stranded nucleic acids was used after being dissolved in distilled water so as to have a concentration of 24 mg/mL (hereinafter referred to as "siRNA solution").

Compound II-1 and sodium 1,2-dimyristoyl-sn-glycero-3-phosphoethanolamine-N-(methoxy(polyethylene glycol)-2000) (PEG-DMPE Na, N-(carbonylmethoxypolyethylene glycol 2000)-1,2-dimyristoyl-sn-glycero-3-phosphoethanolamine sodium salt, manufactured by NOF Corporation) were suspended in a proportion of 57.3/5.52 mmol/L in an aqueous solution containing hydrochloric acid and ethanol, and stirring with a vortex mixer and heating were repeated, thereby obtaining a homogenous suspension. This suspension was allowed to pass through a 0.2-μm polycarbonate membrane filter and a 0.05-μm polycarbonate membrane filter at room temperature, thereby obtaining a dispersion liquid of lead particles. An average particle diameter of the lead particles obtained was measured by means of a dynamic light scattering (DLS) particle size analyzer (Zetasizer Nano ZS, manufactured by Malvern) and confirmed to fall within the range of from 30 nm to 100 nm. The siRNA solution was mixed with the obtained dispersion liquid of lead particles in a proportion of 3/1 (=the dispersion liquid of lead particles/the siRNA solution), to which was then added distilled water in an amount of three times, and the contents were mixed to prepare a dispersion liquid of cationic lipid/double-stranded nucleic acid complex particles.

On the other hand, each lipid was weighed in a proportion of Compound II-1 to Compound I-3 to sodium 1,2-distearoyl-sn-glycero-3-phosphoethanolamine-N-(methoxy (polyethylene glycol)-2000) (PEG-DSPE Na, N-(carbonylmethoxy polyethylene glycol 2000)-1,2-distearoyl-sn-glycro-3-phosphoethanolamine sodium salt, manufactured by NOF Corporation) to distearoyl phosphatidylcholine (DSPC, 1,2-distearoyl-sn-glycero-3-phosphocholine, manufactured by NOF Corporation) to cholesterol (manufactured by NOF Corporation) of 2.98/5.97/2.94/5.71/11.8 mmol/L and dissolved in 90 vol % ethanol, thereby preparing a solution of lipid membrane constituent components.

The obtained solution of lipid membrane constituent components was heated and then mixed with the obtained dispersion liquid of cationic lipid/double-stranded nucleic acid complex particle in a proportion of 1/1. The mixture was further mixed with distilled water in an amount of several times, thereby obtaining a crude preparation.

The obtained crude preparation was concentrated using Amicon Ultra (manufactured by Millipore Corporation), further replaced the solvent with a saline, and then filtered with a 0.2-μm filter (manufactured by Toyo Roshi Kaisha, Ltd.) within a clean bench. Furthermore, an siRNA concentration of the obtained preparation was measured, and the preparation was diluted with a saline such that the siRNA concentration was 1.0 mg/mL, thereby obtaining a preparation 1-A to C (composition containing Compound II-1 and Compound I-3 as the lipids and siRNA A, B or C as the double-stranded nucleic acid). An average particle diameter of lipid particles in the preparation was measured using the particle size analyzer. The results are shown in Table 4.

TABLE 4

| preparation | 1-A | 1-B | 1-C |
|---|---|---|---|
| siRNA | A | B | C |
| particle size (nm) | 94 | 95 | 93 |

Example 2

A preparation was produced in the following manner by using Compound II-1 obtained in Referential Example 1 and Compound I-3 obtained in Referential Example 11 and also using siRNA Nos. A, D or E in Table 3.

Each of the double-stranded nucleic acids was used after being dissolved in distilled water so as to have a concentration of 24 mg/mL (hereinafter referred to as "siRNA solution").

Compound II-1 and PEG-DSPE Na were suspended in a proportion of 57.3/5.52 mmol/L in an aqueous solution containing hydrochloric acid and ethanol, and stirring with a vortex mixer and heating were repeated, thereby obtaining a homogenous suspension. This suspension was allowed to pass through a 0.2-μm polycarbonate membrane filter and a 0.05-μm polycarbonate membrane filter at room temperature, thereby obtaining a dispersion liquid of lead particles. An average particle diameter of the lead particles obtained was measured by means of a particle size analyzer and confirmed to fall within the range of from 30 nm to 100 nm. The siRNA solution was mixed with the obtained dispersion liquid of lead particles in a proportion of 3/1 (=the dispersion liquid of lead particles/the siRNA solution), to which was then added distilled water in an amount of three times, and the contents were mixed to prepare a dispersion liquid of cationic lipid/double-stranded nucleic acid complex particles.

On the other hand, each lipid was weighed in a proportion of Compound II-1 to Compound I-3 to PEG-DSPE Na to DSPC to cholesterol of 2.98/5.97/2.94/5.71/11.8 mmol/L and dissolved in 90 vol % ethanol, thereby preparing a solution of lipid membrane constituent components.

The obtained solution of lipid membrane constituent components was heated and then mixed with the obtained dispersion liquid of cationic lipid/double-stranded nucleic acid complex particle in a proportion of 1/1. The mixture was further mixed with distilled water in an amount of several times, thereby obtaining a crude preparation.

The obtained crude preparation was concentrated using Amicon Ultra (manufactured by Millipore Corporation), further replaced the solvent with a saline, and dialyzed against saline with a dialysis membrane (Spectra For Biotech Cellulose Ester membrane, MWCO: 300 KDa, manufactured by Spectrum Laboratories, Inc), and concentrated using Amicon Ultra (manufactured by Millipore Corporation), then filtered with a 0.2-μm filter (manufactured by Toyo Roshi Kaisha, Ltd.) within a clean bench. Furthermore, an siRNA concentration of the obtained preparation was measured, and the preparation was diluted with a saline such that the siRNA concentration was 1.0 mg/mL, thereby obtaining a preparation 2-A, 2-D and 2-E (composition containing Compound II-1 and Compound I-3 as the lipids and siRNA A, D or E as the double-stranded nucleic acid).

An average particle diameter of lipid particles in the preparation was measured using a particle size analyzer. The results are shown in Table 5.

TABLE 5

| preparation | 2-A | 2-D | 2-E |
|---|---|---|---|
| siRNA | A | D | E |
| particle size (nm) | 87 | 86 | 84 |

Example 3

A preparation 3-A (composition containing Compound II-1 and Compound I-3 as the lipids and siRNA A as the double-stranded nucleic acid) was produced in the same manner as Example 1 by using Compound II-1 obtained in Referential Example 1 and Compound I-3 obtained in Referential Example 11 and also using siRNA No A in Table 3, with lead particles being Compound II-1/PEG-DSPE Na=57.3/5.52 mmol/L and with lipid membrane constituent components being Compound II-1/Compound I-3/PEG-DSPE Na/DSPC/Cholesterol=2.98/8.83/3.93/8.83/14.7 mmol/L. An average particle diameter of lipid particles in the preparation measured using a particle size analyzer was 101 nm.

Example 4

A preparation 4-A (composition containing Compound II-1 and Compound I-3 as the lipids and siRNA A as the double-stranded nucleic acid) was produced in the same manner as Example 1 by using Compound II-1 obtained in Referential Example 1 and Compound I-3 obtained in Referential Example 11 and also using siRNA No A in Table 3, with lead particles being Compound II-1/PEG-DSPE Na=57.3/5.52 mmol/L and with of lipid membrane constituent components being Compound II-1/Compound I-3/PEG-DSPE Na/DSPC/Cholesterol=0.736/8.83/2.70/8.83/5.89 mmol/L. An average particle diameter of lipid particles in the preparation measured using a particle size analyzer was 80 nm.

Example 5

A preparation 5-A (composition containing Compound II-1 and Compound I-3 as the lipids and siRNA A as the double-stranded nucleic acid) was produced in the same manner as Example 1 by using Compound II-1 obtained in Referential Example 1 and Compound I-3 obtained in Referential Example 11 and also using siRNA No A in Table 3, with lead particles being Compound II-1/PEG-DSPE Na=57.3/5.52 mmol/L and with lipid membrane constituent components being Compound II-1/Compound I-3/PEG-DSPE Na/DSPC/Cholesterol=2.98/8.83/2.95/8.83/5.89 mmol/L. An average particle diameter of lipid particles in the preparation measured using a particle size analyzer was 79 nm.

Example 6

A preparation 6-A (composition containing Compound II-1 and Compound I-3 as the lipids and siRNA A as the double-stranded nucleic acid) was produced in the same manner as Example 1 by using Compound II-1 obtained in Referential Example 1 and Compound I-3 obtained in Referential Example 11 and also using siRNA No A in Table 3, with lead particles being Compound II-1/PEG-DSPE Na=57.3/5.52 mmol/L and with lipid membrane constituent components being Compound II-1/Compound I-3/PEG-DSPE Na/DSPC/Cholesterol=0.736/8.83/3.68/8.83/14.7 mmol/L. An average particle diameter of lipid particles in the preparation measured using a particle size analyzer was 98 nm.

Example 7

A preparation 7-A (composition containing Compound I-3 as the lipid and siRNA A as the double-stranded nucleic acid) was produced in the same manner as Example 1 by using Compound I-3 obtained in Referential Example 1 and also using siRNA No A in Table 3, with lead particles being Compound I-3/PEG-DSPE Na=57.3/5.52 mmol/L and with lipid membrane constituent components being Compound I-3/PEG-DSPE Na/DSPC/Cholesterol 8.95/2.94/5.71/11.8 mmol/L. An average particle diameter of lipid particles in the preparation measured using a particle size analyzer was 92 nm.

Test Example 1

The preparation 1-A to C obtained in Example 1 (composition containing Compound II-1 and Compound I-3 as the lipids and siRNA A to C as the double-stranded nucleic acid) was subjected to an in vivo mRNA knockdown evaluation test in the following manner.

MIA PaCa-2 that is a cell line derived from human pancreas cancer was received from the JCRB Cell Bank and cultivated with high glucose-containing DMEM medium (manufactured by GIBCO, 11995-065) containing a 10% inactivated fetal calf serum (manufactured by GIBCO) and 1 vol % penicillin-streptomycin (manufactured by GIBCO, 15140-122) under conditions at 37° C. and 5% $CO_2$. MIA PaCa-2 was suspended in Phosphate buffered saline (PBS) in a concentration of $8 \times 10^7$ cells/mL, and 100 μL of this cell suspension was transplanted into a dorsal subcutis of SCID mouse (delivered from Harlan Labs.) ($8 \times 10^6$ cells/0.1 mL PBS/head). Five days after the transplantation, the mice were divided into groups consisting of five heads per group while taking the tumor volume as an index, and each of the preparations 1-A to C obtained in Example 1 was intravenously administered in an amount equivalent to 10 mg/kg siRNA. As a saline-administered group, a saline was administered in a dose of 10 mL/kg. Before the administration and 48 hours after the administration, the weight of the mouse was measured. After the weight measurement, the mouse was euthanized, and the subcutaneous tumor was removed. The removed tumor was immediately frozen by liquid nitrogen and stored at −80° C. until it was used.

With respect to the obtained tumor sample, 1 mL of a Trizol reagent (manufactured by Invitrogen, 10296-028) and Stainless Steel Beads (manufactured by QIAGEN, 69989) of 5 mm were added to a 2-mL round bottom tube containing the sample charged therein, and the contents were pulverized by Tissue lyser II (manufactured by QIAGEN) under conditions of 1/25 freq, 1.5 minutes x 2 times. After the pulverization, centrifugation (at 10,000 rpm for 10 minutes) was conducted, the supernatant was recovered, to which was then added 200 μL of chloroform, and the contents were vigorously stirred, followed by again conducting centrifugation (at 15,000 rpm for 15 min). To the obtained supernatant, the same amount of a 70% ethanol solution was added, the contents were mixed, and the mixture was applied to an RNeasy Mini Kit spin column (manufactured by QIAGEN) and subjected to centrifugation (8,000×g for 15 seconds). A filtrate was discarded, 700 µL of an RNeasy Mini Kit RW1 (manufactured by QIAGEN) was added to the residue, and the contents were subjected to centrifugation (8,000×g for 15 seconds). A filtrate was discarded, 500 µL of an RNeasy Mini Kit RPE (manufactured by QIAGEN) was newly added to the residue, and the contents were subjected to centrifugation (8,000×g for 15 seconds). A filtrate was discarded, 500 µL of the RNeasy Mini Kit RPE was again added to the residue, and the contents were subjected to centrifugation (8,000×g for 2 minutes). A filtrate was discarded, and the residue was further subjected to centrifugation (at 15,000 rpm for one minute) to remove the solution within the column. To the RNeasy spin column, 30 µL of RNase free water was added, and the contents were subjected to centrifugation (8,000×g for one minute) to extract RNA. A concentration of the extracted RNA was measured by an absorption photometer, Spectra Max M3 (manufactured by Molecular Devices), and RNA corresponding to from 500 to 1,000 ng was subjected to reverse transfer with a Transcriptor (manufactured by Roche, 4897030). The reaction solution and the reaction condition followed those described in the instruction manual attached to Transcriptor. The obtained cDNA sample was diluted ten times with $dH_2O$ and used as a template of qPCR. For the qPCR reaction, TaqMan Gene Expression Master Mix (manufactured by Applied Biosystems, 4369542) and TaqMan Gene Expression Assays (manufactured by Applied Biosystems, 4331182) were used. The conditions of the PCR reaction followed those described in the instruction manual attached to the TaqMan Gene Expression. A mRNA amount of the specimen was calculated as a relative proportion when the mRNA amount of KRAS was defined as 1.

FIG. 1 shows the amount of KRAS mRNA in tumor.

As is clear from FIG. 1, the results of the in vivo pharmacological evaluation test revealed that in each of the preparations obtained in Example 1, the expression of the KRAS gene was extremely strongly inhibited.

Test Example 2

Each of the preparations 1-A to C obtained in Example 1 (lipid particles containing Compound II-1 and Compound I-3 as the lipids and siRNA No. A to C as the double-stranded nucleic acid) was subjected to a tumor proliferation evaluation test in the following manner.

Similar to Test Example 1, the test was carried out using a xenograft model in which MIA PaCA-2 that is a cell line derived from human pancreas cancer was transplanted in an SCID mouse. The mice were divided into groups consisting of seven heads per group while taking the tumor volume as an index (Day 0), and each of the preparations 1-A to C obtained in Example 1 was intravenously administered to the mouse in an amount equivalent to 10 mg/kg siRNA on Day 0 and Day 7, respectively. As a saline-administered group, a saline was administered in a dose of 10 mL/kg. A tumor size of each individual was measured on from Day 0 to Day 17, and a tumor volume and a volume ratio were calculated according to the following equations. And, a body weight of each individual was measured on from Day 0 to Day 17.

Tumor volume ($mm^3$)=Major axis (mm)×Minor axis (mm)×Minor axis (mm)×0.5

Volume ratio ($V/V0$)=Tumor volume at each point of time ($mm^3$)÷Tumor volume on Day 0 ($mm^3$)

FIG. 2 shows the transition of a relative value of the tumor volume.

As is clear from FIG. 2, the results of the in vivo pharmacological evaluation test revealed that each of the preparations 1-A to C obtained in Examples 1 has a strong antitumor action.

Accordingly, it has become clear that when the composition of the present invention is administered to mammals, it is able to reduce the expression of a RAS gene in a living body, thereby treating the RAS-associated diseases.

Test Example 3

The preparations 1-A and 1-C obtained in Example 1 (composition containing Compound II-1 and Compound I-3 as the lipids and siRNA A or C as the double-stranded nucleic acid) were intravenously administered to mice twice with 7-day interval and the blood concentrations of siRNAs were compared between the first and second injections.

The preparation 1-A or 1-C obtained in Example 1 was administered to male CD1 mice (6 weeks of age, CHARLES RIVER LABORATORIES JAPAN, INC.) via tail vein in an amount equivalent to 10 mg siRNA/kg. 7 days after the first injection, the second injections were performed in the same way as the first injections. 20 µL of blood was collected from tail artery at 0.5, 2, 6 and 24 hours after both first and second injection, and mixed with 100 µL of a denaturing solution (4 mol/L guanidine thiocyanate, 25 mmol/L sodium citrate, 1 mmol/L dithiothreitol, 0.5 w/v % sodium N-lauroyl sarcosine).

The obtained solutions were mixed with internal standard and Phenol:Chloroform:Isoamyl Alcohol pH 8.0 (Invitrogen) and then centrifuged. The supernatants were mixed with GenTLE precipitation carrier (Takara Bio Inc.) and sodium acetate, and then mixed with ethanol. After centrifugation, the supernatants were discarded, and 75 v/v % ethanol was added to the precipitates. After centrifugation, the supernatants were discarded. The precipitates were air-dried, dissolved in distilled water and subjected to LC/MS analysis to measure blood concentrations of both sense and antisense strands.

Apparatus
HPLC apparatus: ACQUITY HPLC system (Waters)
Mass spectrometer: TQ Detector (Waters)
HPLC Conditions
Internal Standard
Duplex of the following sequences, 5'-mGmUrAmUrUmUrGmCrGrUrAmUrUmUrAmUrUmArUrGrUrAmA-dAdT-3' (SEQ ID NO: 12) 5'-mAmUmUmUrArCrArUrA-rAmUmAmArArUrArCrGrCrArArArUrAmCrAmC-3' (SEQ ID NO: 13) (the sugars binding to the bases prefaced by m and r are 2'-O-methyl-substituted ribose and ribose, respectively)
Column: ACQUITY UPLC OST C18 (1.7 µm, 2.1 mm I.D.×100 mm, Waters)
Column temperature: 70° C.
Mobile Phase:
A solution 15 mmol triethylamine, 400 mmol hexafluoroisopropyl alcohol in water
B Solution Methanol
Gradient: B concentration was linearly raised from 10% to 25% in 9 minutes.
Flow rate: 0.4 mL/min The time courses of blood concentrations after first and second injection were almost similar for both the preparations 1-A and 1-C of Examples 1.

Test Example 4

The preparations 1-A to C obtained in Example 1 (composition containing Compound II-1 and Compound I-3 as the lipids and siRNA A to C as the double-stranded nucleic acid) were used for the evaluation of anti-PEG antibody production in vivo, as follows.

BALB/c mice (provided by Harlan Labs) were randomly divided into groups of three, and each preparations obtained in Example 1 was intravenously administered to the mice in an amount equivalent to 10 mg/kg siRNA. As a saline-administered group, a saline was administered in a dose of 10 mL/kg. The mice were anesthetized using isoflurane 1 week after the administration. Following laparotomy, blood (about 500 μL) was collected through the abdominal portion of vena cava. The collected blood was placed in a tube containing a blood serum separating medium, and left unattended for 30 min at room temperature. After 10-min centrifugation at 3,000 rpm, the collected serum was stored at −20° C. until use.

Biotin-PEG (Nanocs Inc., PEGS-0001; 50 μL) diluted in PBS (40 μg/mL) was added to an avidin-coated plate (Thermo Fisher Scientific Inc. (Nunc), 236001). Biotin-PEG was not added to the wells for adding the standard. After being left unattended for about 1 hour at room temperature, the plate was washed three times with Tris-Buffered Saline Tween-20 (TBST). A serum sample (50 μL) diluted 50 times with 1% bovine serum albumin (BSA)-containing PBS was then added to the wells containing the Biotin-PEG. For the wells containing no Biotin-PEG, Biotin-mouse anti-human CCR4 antibodies (BD Biosciences, 551266; 50 μL) were added as the standard (0.98 to 62.5 pg/mL). After being unattended for about 2 hours at room temperature, the plate was washed four times with TEST. Then, POD conjugated anti-mouse IgGAM antibodies (ICN/Cappel, 55570; 50 μL) diluted 5,000 times with 1% BSA-containing PBS were added to the all wells. The plate was washed four times with TBST after being left unattended for about 2 hours at room temperature. Thereafter, a TMB Substrate Reagent Set (BD Biosciences, 555214; 50 μL) was added. The samples were left unattended for about 30 min in the dark at room temperature, and the enzyme reaction was stopped by addition of 50 μL of 1M-$H_2SO_4$. Absorbance at 450 nm and 620 nm were measured with a plate reader, and the relative anti-PEG antibody amounts of the samples were calculated from the standard curve of the standard sample. FIG. 3 shows the blood anti-PEG antibody amounts.

Test Example 5

The preparations 2-A, 2-D, and 2-E obtained in Example (composition containing Compound II-1 and Compound I-3 as the lipids and siRNA A, D or E as the double-stranded nucleic acid) were used to conduct an in vivo mRNA knockdown evaluation test, as follows.

The test was conducted with a xenograft model created by transplanting the human pancreatic cancer-derived cell line MIA PaCa-2 into SCID mice (provided by CLEA Japan), as in Test Example 1. The mice were divided into groups of three by using the tumor volume as an index (Day 0), and each preparations obtained in Example 2 was administered in an amount equivalent to 10 mg/kg, 3 mg/kg, or 1 mg/kg siRNA on Day 0. As a saline-administered group, a saline was administered in a dose of 10 mL/kg. As in Test Example 1, the tumor samples were disrupted, and centrifuged to collect the supernatant. After adding chloroform, the supernatant was vigorously stirred, and recentrifuged (15,000 rpm, 15 min). RNA was extracted from the resulting supernatant (200 μL) using a Cellular RNA Large Volume Kit (Roche, 5467535) with an automatic nucleic acid extractor MagNA PURE 96 (Roche). As in Test Example 1, the mRNA levels of the extracted RNA samples were calculated as the relative proportions with respect to the KRAS mRNA level 1 of the saline-administered group. FIG. 4 shows the amount of KRAS mRNA in tumor.

As is clear from FIG. 4, the result of the in vivo efficacy evaluation test revealed that the preparations obtained in Example 2 were highly capable of inhibiting the KRAS gene expression.

Test Example 6

The preparations 2-A, 2-D, and 2-E obtained in Example 2 (composition containing Compound II-1 and Compound I-3 as the lipids and siRNA A, D or E as the double-stranded nucleic acid) were used to conduct a tumor growth evaluation test, as follows.

The test was conducted with a xenograft model created by transplanting the human pancreatic cancer-derived cell line MIA PaCa-2 into SCID mice (provided by CLEA Japan), as in Test Example 2. The mice were divided into groups of five by using the tumor volume as an index (Day 0), and each preparation obtained in Example 2 was intravenously administered in an amount equivalent to 10 mg/kg, 3 mg/kg, or 1 mg/kg siRNA on Day 0. As a saline-administered group, a saline was administered in a dose of 10 mL/kg. The tumor size of each individual was measured on Day 7, and the tumor volume and the volume ratio were calculated according to the methods used in Test Example 2. FIG. 5 shows the relative value of the tumor volume.

As is clear from FIG. 5, the results of the in vivo efficacy evaluation test revealed that the preparations obtained in Example 2 had strong anti-tumor activity.

The results therefore demonstrated that the composition of the present invention can be administered to mammals to lower RAS gene expression in the organism and treat RAS-related diseases.

Test Example 7

The preparation 1-A obtained in Example 1, and the preparation 2-A obtained in Example 2 (composition containing Compound II-1 and Compound I-3 as the lipids and siRNA A as the double-stranded nucleic acid) were used to conduct a tumor growth evaluation test, as follows.

The test was conducted with a xenograft model created by transplanting the human pancreatic cancer-derived cell line MIA PaCa-2 into SCID mice (provided by CLEA Japan), as in Test Example 2. The mice were divided into groups of five by using the tumor volume as an index (Day 0), and each preparation was intravenously administered in an amount equivalent to 2.5 mg/kg siRNA on Day 0. As a saline-administered group, a saline was administered in a dose of 10 mL/kg. The tumor size of each individual was measured on Day 7, and the tumor volume and the volume ratio were calculated according to the methods used in Test Example 2. FIG. 6 shows the relative value of the tumor volume.

Test Example 8

The preparation 1-A obtained in Example 1, the preparation 3-A obtained in Example 3, and the preparation 4-A obtained in Example 4 (composition containing Compound II-1 and Compound I-3 as the lipids and siRNA A as the double-stranded nucleic acid) were used to conduct a tumor growth evaluation test according to the method used in Test Example 7. FIG. 7 shows the relative value of the tumor volume.

Test Example 9

The preparation 1-A obtained in Example 1, the preparation 5-A obtained in Example 5, and the preparation 6-A obtained in Example 6 (composition containing Compound II-1 and Compound I-3 as the lipids and siRNA A as the double-stranded nucleic acid) were used to conduct a tumor growth evaluation test according to the method used in Test Example 7. FIG. 8 shows the relative value of the tumor volume.

Test Example 10

The preparation 1-A obtained in Example 1 (composition containing Compound II-1 and Compound I-3 as the lipids and siRNA A as the double-stranded nucleic acid), and the preparation 7-A obtained in Example 7 (composition containing Compound I-3 as the lipids and siRNA A as the double-stranded nucleic acid) were used to conduct a tumor growth evaluation test, as follows.

The test was conducted with a xenograft model created by transplanting the human pancreatic cancer-derived cell line MIA PaCa-2 into SCID mice (provided by CLEA Japan), as in Test Example 2. The mice were divided into groups of five by using the tumor volume as an index (Day 0), and each preparation was intravenously administered in an amount equivalent to 5 mg/kg siRNA on Day 0. As a saline-administered group, a saline was administered in a dose of 10 mL/kg. The tumor size of each individual was measured on Day 7, and the tumor volume and the volume ratio were calculated according to the methods used in Test Example 2. FIG. 9 shows the relative value of the tumor volume.

Test Example 10

The preparation 1-A obtained in Example 1 (composition containing Compound II-1 and Compound I-3 as the lipids and siRNA A as the double-stranded nucleic acid) were used to conduct a tumor growth evaluation test, as follows.

The test was conducted with a xenograft model created by transplanting the human colorectal cancer-derived cell line HCT116 (ATCC) into SCID mice (provided by CLEA Japan), as in Test Example 2. The mice were divided into groups of five by using the tumor volume as an index (Day 0), and each preparation was intravenously administered in an amount equivalent to 10 mg/kg siRNA on Day 0 and Day 7. As a saline-administered group, a saline was administered in a dose of 10 mL/kg. The tumor size of each individual was measured on Day 0 to 17, and the tumor volume and the volume ratio were calculated according to the methods used in Test Example 2. FIG. 10 shows the transition of the relative value of the tumor volume.

INDUSTRIAL APPLICABILITY

A RAS-associated disease can be treated by administrating the composition of the present invention to a mammal, thereby suppressing the expression of a KRAS gene in a living body.

SEQUENCE LISTING FREE TEXT

SEQ No. 1: Target in KRAS mRNA
SEQ No. 2: Target in KRAS mRNA
SEQ No. 3: Target in KRAS mRNA
SEQ No. 4: siRNA sense
SEQ No. 5: siRNA antisense
SEQ No. 6: siRNA sense
SEQ No. 7: siRNA antisense
SEQ No. 8: siRNA sense
SEQ No. 9: siRNA antisense
SEQ No. 10: siRNA antisense
SEQ No. 11: siRNA antisense
SEQ No. 12: IS for siRNA sense
SEQ No. 13: IS for siRNA antisense

SEQUENCE LISTING

1001P12225 Sequence Listing.txt

---

The invention claimed is:

1. A composition comprising a lipid particle containing, as a drug, a double-stranded nucleic acid having a sense strand and an antisense strand, each consisting of SEQ ID NOs:4 and 5 respectively, SEQ ID NOs:6 and 7 respectively, SEQ ID NOs:8 and 9 respectively, SEQ ID NOs:4 and 10 respectively, or SEQ ID NOs:4 and 11 respectively; and a cationic lipid having the following formula (I):

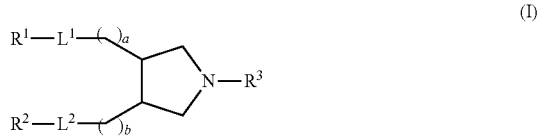

(I)

wherein
$R^1$ and $R^2$ are each linear or branched alkenyl having a carbon number of from 12 to 24;
$L^1$ and $L^2$, which are the same or different, are each —CO—O— or —O—CO—;
a and b, which are the same or different, are each 1; and
$R^3$ is a hydrogen atom, or alkyl having a carbon number of from 1 to 6; and a cationic lipid having the following formula (II):

(II)

wherein
$R^4$ and $R^5$ are each linear or branched alkenyl having a carbon number of from 12 to 24; and
$R^6$ is a hydrogen atom, or alkyl having a carbon number of from 1 to 6.

2. The composition according to claim 1, wherein $R^4$ and $R^5$ are identically (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, or 3,7,11,15-tetramethylhexadec-2-enyl.

3. The composition according to claim 1, wherein $R^4$ and $R^5$ are identically (Z)-hexadec-9-enyl, (Z)-octadec-6-enyl, (Z)-octadec-9-enyl, (9Z,12Z)-octadeca-9,12-dienyl, (Z)-icos-11-enyl, or (11Z,14Z)-icosa-11,14-dienyl.

4. The composition according to claim 2, wherein $R^6$ is a hydrogen atom, or methyl.

5. The composition according to claim 1, wherein $R^3$ is a hydrogen atom or methyl.

6. The composition according to claim 1, wherein $L^1$ and $L^2$ are each —O—CO—; and $R^1$ and $R^2$ are identically (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, or 3,7,11,15-tetramethylhexadec-2-enyl.

7. The composition according to claim 1, wherein $L^1$ and $L^2$ are each —CO—O—; and $R^1$ and $R^2$ are identically (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-heptadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl, or 2,6,10,14-tetramethylpentadec-1-enyl.

8. The composition according to claim 1, wherein the cationic lipid forms a complex together with the double-stranded nucleic acid, or forms a complex between a combination of the cationic lipid with a neutral lipid and/or a polymer and the double-stranded nucleic acid.

9. The composition according to claim 1, wherein the cationic lipid forms a complex together with the double-stranded nucleic acid, or forms a complex between a combination of the cationic lipid with a neutral lipid and/or a polymer and the double-stranded nucleic acid, and the lipid particle is constituted of the complex and a lipid membrane for encapsulating the complex.

10. A method for suppressing the expression of a RAS gene comprising, introducing the double-stranded nucleic acid into a cell by using the composition as set forth above in claim 1.

11. The method according to claim 10, wherein the cell is a cell present in tumor of a mammal.

12. The method according to claim 10, wherein the cell is a cell present in a large intestine or a pancreas of a mammal.

13. The method according to claim 10, wherein the method of the introduction into a cell is a method of introduction into a cell by intravenous administration.

14. A method for treating a RAS-associated disease comprising administering the composition according to claim 1 to a mammal.

15. The method according to claim 14, wherein the method of the administration is intravenous administration.

16. A method for treating a cancer comprising administering the composition according to claim 1 to a mammal.

17. The method according to claim 16, wherein the method of the administration is intravenous administration.

18. A medicine comprising the composition according to claim 1, for the use in treating a RAS-associated disease.

19. The medicine according to claim 18, which is for intravenous administration.

20. A therapeutic agent for cancer comprising the composition according to claim 1.

21. The therapeutic agent for cancer according to claim 20, which is for intravenous administration.

* * * * *

SEQUENCE LISTING

<160> NUMBER OF SEQ ID NOS: 13

<210> SEQ ID NO 1
<211> LENGTH: 21
<212> TYPE: RNA
<213> ORGANISM: Homo sapiens

<400> SEQUENCE: 1
guguauuugc cauaaauaau a                                      21

<210> SEQ ID NO 2
<211> LENGTH: 21
<212> TYPE: RNA
<213> ORGANISM: Homo sapiens

<400> SEQUENCE: 2
uacuaaauca uuugaagaua u                                      21

<210> SEQ ID NO 3
<211> LENGTH: 21
<212> TYPE: RNA
<213> ORGANISM: Homo sapiens

<400> SEQUENCE: 3
auacuaaauc auuugaagau a                                              21

<210> SEQ ID NO 4
<211> LENGTH: 25
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (1)..(23)
<223> OTHER INFORMATION: RNA
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
<221> NAME/KEY: misc_feature
<222> LOCATION: (4)..(4)
<223> OTHER INFORMATION: n = uracil
<220> FEATURE:
<221> NAME/KEY: modified_base
<222> LOCATION: (4)..(4)
<223> OTHER INFORMATION: um
<220> FEATURE:
<221> NAME/KEY: misc_feature
<222> LOCATION: (5)..(5)
<223> OTHER INFORMATION: n = uracil
<220> FEATURE:
<221> NAME/KEY: misc_feature
<222> LOCATION: (6)..(6)
<223> OTHER INFORMATION: n = uracil
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: cm
<220> FEATURE:
<221> NAME/KEY: misc_feature
<222> LOCATION: (11)..(11)
<223> OTHER INFORMATION: n = uracil
<220> FEATURE:
<221> NAME/KEY: modified_base
<222> LOCATION: (12)..(12)
<223> OTHER INFORMATION: am
<220> FEATURE:
<221> NAME/KEY: modified_base
<222> LOCATION: (14)..(14)
<223> OTHER INFORMATION: am
<220> FEATURE:
<221> NAME/KEY: misc_feature
<222> LOCATION: (15)..(15)
<223> OTHER INFORMATION: n = uracil
<220> FEATURE:
<221> NAME/KEY: modified_base
<222> LOCATION: (16)..(16)
<223> OTHER INFORMATION: am
<220> FEATURE:
<221> NAME/KEY: misc_feature
<222> LOCATION: (18)..(18)
<223> OTHER INFORMATION: n = uracil
<220> FEATURE:
<221> NAME/KEY: modified_base
<222> LOCATION: (18)..(18)

-continued

```
<223> OTHER INFORMATION: um
<220> FEATURE:
<221> NAME/KEY: misc_feature
<222> LOCATION: (21)..(21)
<223> OTHER INFORMATION: n = uracil
<220> FEATURE:
<221> NAME/KEY: modified_base
<222> LOCATION: (23)..(23)
<223> OTHER INFORMATION: am

<400> SEQUENCE: 4
gnannngcca naaanaanac naaat                                              25

<210> SEQ ID NO 5
<211> LENGTH: 27
<212> TYPE: RNA
<213> ORGANISM: Artificial Sequence
<220> FEATURE:
<223> OTHER INFORMATION: siRNA antisense
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(4)
<223> OTHER INFORMATION: um
<220> FEATURE:
<221> NAME/KEY: modified_base
<222> LOCATION: (11)..(11)
<223> OTHER INFORMATION: am
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (27)..(27)
<223> OTHER INFORMATION: cm

<400> SEQUENCE: 5
auuuaguauu auuuauggca aauacac                                            27

<210> SEQ ID NO 6
<211> LENGTH: 25
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (1)..(23)
<223> OTHER INFORMATION: RNA
<220> FEATURE:
<221> NAME/KEY: modified_base
<222> LOCATION: (1)..(1)
<223> OTHER INFORMATION: cm
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: am
<220> FEATURE:
<221> NAME/KEY: misc_feature
```

```
<222> LOCATION: (6)..(6)
<223> OTHER INFORMATION: n = uracil
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: am
<220> FEATURE:
<221> NAME/KEY: misc_feature
<222> LOCATION: (9)..(11)
<223> OTHER INFORMATION: n = uracil
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: am
<220> FEATURE:
<221> NAME/KEY: modified_base
<222> LOCATION: (16)..(16)
<223> OTHER INFORMATION: am
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (18)..(18)
<223> OTHER INFORMATION: am
<220> FEATURE:
<221> NAME/KEY: misc_feature
<222> LOCATION: (19)..(19)
<223> OTHER INFORMATION: n = uracil
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: n = uracil
<220> FEATURE:
<221> NAME/KEY: modified_base
<222> LOCATION: (23)..(23)
<223> OTHER INFORMATION: cm

<400> SEQUENCE: 6
cnaaancann ngaaganann cacca                                      25

<210> SEQ ID NO 7
<211> LENGTH: 27
<212> TYPE: RNA
<213> ORGANISM: Artificial Sequence
<220> FEATURE:
<223> OTHER INFORMATION: siRNA antisense
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: am
<220> FEATURE:
```

```
<221> NAME/KEY: modified_base
<222> LOCATION: (17)..(17)
<223> OTHER INFORMATION: am
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: gm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(27)
<223> OTHER INFORMATION: am

<400> SEQUENCE: 7
uggugaauau cuucaaauga uuuagua                                        27

<210> SEQ ID NO 8
<211> LENGTH: 25
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (1)..(23)
<223> OTHER INFORMATION: RNA
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(2)
<223> OTHER INFORMATION: cm
<220> FEATURE:
<221> NAME/KEY: misc_feature
<222> LOCATION: (3)..(3)
<223> OTHER INFORMATION: n = uracil
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (10)..(12)
<223> OTHER INFORMATION: n = uracil
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: am
<220> FEATURE:
<221> NAME/KEY: misc_feature
<222> LOCATION: (18)..(18)
<223> OTHER INFORMATION: n = uracil
```

```
<220> FEATURE:
<221> NAME/KEY: modified_base
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n = uracil

<400> SEQUENCE: 8
acnaaancan nngaaganan ncacc                                              25

<210> SEQ ID NO 9
<211> LENGTH: 27
<212> TYPE: RNA
<213> ORGANISM: Artificial Sequence
<220> FEATURE:
<223> OTHER INFORMATION: siRNA antisense
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (23)..(23)
<223> OTHER INFORMATION: am
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (27)..(27)
<223> OTHER INFORMATION: um

<400> SEQUENCE: 9
ggugaauauc uucaaaugau uuaguau                                            27

<210> SEQ ID NO 10
<211> LENGTH: 27
<212> TYPE: RNA
<213> ORGANISM: Artificial Sequence
<220> FEATURE:
<223> OTHER INFORMATION: siRNA antisense
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(4)
<223> OTHER INFORMATION: um
<220> FEATURE:
<221> NAME/KEY: modified_base
<222> LOCATION: (11)..(11)
<223> OTHER INFORMATION: am
<220> FEATURE:
<221> NAME/KEY: modified_base
<222> LOCATION: (13)..(13)
```

```
<223> OTHER INFORMATION: um
<220> FEATURE:
<221> NAME/KEY: modified_base
<222> LOCATION: (21)..(21)
<223> OTHER INFORMATION: am
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: am
<220> FEATURE:
<221> NAME/KEY: modified_base
<222> LOCATION: (27)..(27)
<223> OTHER INFORMATION: cm

<400> SEQUENCE: 10
auuuaguauu auuuauggca aauacac                                             27

<210> SEQ ID NO 11
<211> LENGTH: 27
<212> TYPE: RNA
<213> ORGANISM: Artificial Sequence
<220> FEATURE:
<223> OTHER INFORMATION: siRNA antisense
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(4)
<223> OTHER INFORMATION: um
<220> FEATURE:
<221> NAME/KEY: modified_base
<222> LOCATION: (11)..(11)
<223> OTHER INFORMATION: am
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: am
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: am
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: am
<220> FEATURE:
<221> NAME/KEY: modified_base
```

```
<222> LOCATION: (27)..(27)
<223> OTHER INFORMATION: cm

<400> SEQUENCE: 11
auuuaguauu auuuauggca aauacac                                          27

<210> SEQ ID NO 12
<211> LENGTH: 25
<212> TYPE: DNA
<213> ORGANISM: Artificial Sequence
<220> FEATURE:
<223> OTHER INFORMATION: IS for siRNA sense
<220> FEATURE:
<221> NAME/KEY: misc_feature
<222> LOCATION: (1)..(23)
<223> OTHER INFORMATION: RNA
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
<221> NAME/KEY: misc_feature
<222> LOCATION: (4)..(4)
<223> OTHER INFORMATION: n = uracil
<220> FEATURE:
<221> NAME/KEY: modified_base
<222> LOCATION: (4)..(4)
<223> OTHER INFORMATION: um
<220> FEATURE:
<221> NAME/KEY: misc_feature
<222> LOCATION: (5)..(5)
<223> OTHER INFORMATION: n = uracil
<220> FEATURE:
<221> NAME/KEY: misc_feature
<222> LOCATION: (6)..(6)
<223> OTHER INFORMATION: n = uracil
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: cm
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (12)..(12)
<223> OTHER INFORMATION: n = uracil
<220> FEATURE:
<221> NAME/KEY: modified_base
<222> LOCATION: (12)..(12)
<223> OTHER INFORMATION: um
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
```

```
<222> LOCATION: (14)..(14)
<223> OTHER INFORMATION: n = uracil
<220> FEATURE:
<221> NAME/KEY: modified_base
<222> LOCATION: (14)..(14)
<223> OTHER INFORMATION: um
<220> FEATURE:
<221> NAME/KEY: misc_feature
<222> LOCATION: (16)..(16)
<223> OTHER INFORMATION: n = uracil
<220> FEATURE:
<221> NAME/KEY: modified_base
<222> LOCATION: (16)..(16)
<223> OTHER INFORMATION: um
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (18)..(18)
<223> OTHER INFORMATION: am
<220> FEATURE:
<221> NAME/KEY: misc_feature
<222> LOCATION: (19)..(19)
<223> OTHER INFORMATION: n = uracil
<220> FEATURE:
<221> NAME/KEY: misc_feature
<222> LOCATION: (21)..(21)
<223> OTHER INFORMATION: n = uracil
<220> FEATURE:
<221> NAME/KEY: modified_base
<222> LOCATION: (23)..(23)
<223> OTHER INFORMATION: am

<400> SEQUENCE: 12
gnannngcgn annnannang naaat                                          25

<210> SEQ ID NO 13
<211> LENGTH: 27
<212> TYPE: RNA
<213> ORGANISM: Artificial Sequence
<220> FEATURE:
<223> OTHER INFORMATION: IS for siRNA antisense
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(4)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: am
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (27)..(27)
<223> OTHER INFORMATION: cm

<400> SEQUENCE: 13
auuuacauaa uaaauacgca aauacac                                        27
```